US012735648B2

(12) United States Patent
Nierode et al.

(10) Patent No.: US 12,735,648 B2
(45) Date of Patent: Sep. 15, 2026

(54) PYROLYSIS PROCESSES FOR UPGRADING A HYDROCARBON FEED

(71) Applicant: ExxonMobil Chemical Patents Inc., Baytown, TX (US)

(72) Inventors: Mark A. Nierode, Kingwood, TX (US); Rodney S. Smith, Edinburgh (GB); Michael A. Radzicki, Houston, TX (US); Donald J. Norris, London (CA); Kapil Kandel, Humble, TX (US); Tania M. Almazan, Baton Rouge, LA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 179 days.

(21) Appl. No.: 18/692,245

(22) PCT Filed: Oct. 3, 2022

(86) PCT No.: PCT/US2022/077459
§ 371 (c)(1),
(2) Date: Mar. 14, 2024

(87) PCT Pub. No.: WO2023/060035
PCT Pub. Date: Apr. 13, 2023

(65) Prior Publication Data

US 2024/0425768 A1 Dec. 26, 2024

Related U.S. Application Data

(60) Provisional application No. 63/253,155, filed on Oct. 7, 2021.

(51) Int. Cl.

| | |
|---|---|
| ***C10G 55/04*** | (2006.01) |
| ***C07C 4/02*** | (2006.01) |
| ***C10G 25/00*** | (2006.01) |

(52) U.S. Cl.
CPC ................ *C10G 55/04* (2013.01); *C07C 4/02* (2013.01); *C10G 25/00* (2013.01); *C10G 2300/201* (2013.01); *C10G 2400/20* (2013.01)

(58) Field of Classification Search
CPC .. C10G 55/04; C10G 25/00; C10G 2300/201; C10G 2400/20; C10G 25/003;
(Continued)

(56) References Cited

U.S. PATENT DOCUMENTS 4,835,338 A 5/1989 Liu
5,035,732 A 7/1991 McCue, Jr.
(Continued)

FOREIGN PATENT DOCUMENTS

CN 205893119 U 1/2017
JP 2008081417 4/2008
(Continued)

*Primary Examiner* — Ali Z Fadhel
(74) *Attorney, Agent, or Firm* — WOMBLE BOND DICKINSON (US) LLP; Kevin Davis

(57) ABSTRACT

Processes for upgrading a hydrocarbon for a predetermined period of time. The process can include determining an amount of one or more contaminant-containing compositions that will be present in a pyrolysis effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof. In some examples, the process can also include taking one or more steps to allow the hydrocarbon feed to be steam cracked for at least as long as a predetermined period of time, controlling process conditions within one or more separation stages to favor certain product compositions, introducing a predetermined amount of one or more agents into various locations of the process, or any combination thereof.

6 Claims, 4 Drawing Sheets

(58) Field of Classification Search

CPC ........ C10G 33/00; C10G 33/04; C10G 69/06; C10G 70/06; C10G 9/36; C07C 4/02; C02F 2101/345; C02F 2103/365; Y02P 30/40

See application file for complete search history.

(56) References Cited

U.S. PATENT DOCUMENTS 5,090,977 A 2/1992 Strack et al.
5,452,581 A 9/1995 Dinh et al.
5,820,750 A 10/1998 Blum et al.
6,077,985 A 6/2000 Stork
6,086,751 A 7/2000 Bienstock et al.
7,128,827 B2 10/2006 Tallman et al.
7,138,047 B2 11/2006 Stell et al.
7,244,871 B2 7/2007 Stell et al.
7,294,749 B2 11/2007 Verma et al.
7,763,162 B2 7/2010 Strack
7,820,035 B2 10/2010 McCoy et al.
7,846,324 B2 12/2010 Annamalai et al.
7,972,498 B2 7/2011 Buchanan et al.
8,277,639 B2 10/2012 Buchanan et al.
8,684,384 B2 4/2014 Spicer et al.
8,864,977 B2 10/2014 Spicer
9,090,835 B2 7/2015 Beech, Jr. et al.
9,102,884 B2 8/2015 Xu et al.
9,321,003 B2 4/2016 Radzicki et al.
9,637,694 B2 5/2017 Evans et al.
9,657,239 B2 5/2017 Beech, Jr. et al.
9,771,524 B2 9/2017 Xu et al.
9,777,227 B2 10/2017 Soultanidis et al.
9,809,756 B2 11/2017 Soultanidis et al.
9,901,845 B2 2/2018 Radzicki et al.
10,000,710 B2 6/2018 Ferrughelli et al.
10,016,719 B2 7/2018 Symes
10,427,990 B2 * 10/2019 Fournier .................. C07C 4/04
2007/0007171 A1 1/2007 Strack et al.
2012/0006723 A1 1/2012 Davis et al.
2012/0041243 A1 * 2/2012 Senetar .................. C07C 11/04 585/251
2014/0061100 A1 3/2014 Lattner et al.
2015/0361359 A1 12/2015 Beech, Jr. et al.
2017/0029301 A1 2/2017 Arnst et al.
2018/0057759 A1 3/2018 Kandel et al.
2018/0134972 A1 5/2018 Brown et al.
2018/0171239 A1 6/2018 Chen et al.
2019/0375992 A1 12/2019 Karime et al.

FOREIGN PATENT DOCUMENTS

WO 2020/263545 12/2020
WO 2021/161219 8/2021

* cited by examiner

PYROLYSIS PROCESSES FOR UPGRADING A HYDROCARBON FEED

CROSS-REFERENCE TO RELATED APPLICATIONS

This application is a US national phase application of PCT Application Serial No. PCT/US2022/077459 having a filing date of Oct. 3, 2022, which claims priority to and the benefit of U.S. Provisional Application No. 63/253,155 having a filing date of Oct. 7, 2021, the disclosures of all of which are incorporated herein by reference in their entireties.

FIELD

Embodiments disclosed herein generally relate to pyrolysis processes for upgrading a hydrocarbon feed. More particularly, such processes relate to pyrolysis processes for pyrolyzing a hydrocarbon feed that produces a pyrolysis effluent containing one or more contaminant-containing compositions.

BACKGROUND

Pyrolysis processes, e.g., steam cracking, convert saturated hydrocarbons, e.g., paraffins, to higher-value products, e.g., light olefins such as ethylene and propylene. In addition to these higher-value products, however, the pyrolysis process also produces naphtha, gas oil, and a significant amount of relatively low-value heavy products such as pyrolysis tar. In a steam cracking process, a primary separator is typically used to separate the various products, such as a process gas, a steam cracker naphtha (SCN) or "pygas", a steam cracker gas oil (SCGO), a steam cracker quench oil (SCQO), a steam cracker tar (SCT), etc., from a steam cracker effluent.

It has become increasingly desirable to utilize low value raw feedstocks, e.g., a $C_{5+}$ hydrocarbon, as the hydrocarbon feed to the pyrolysis unit, e.g., steam cracker. While these raw feedstocks are attractive from a cost standpoint, such feedstocks can introduce significant levels of contaminant-containing compositions, e.g., oxygenates, into the pyrolysis process that typically have not been a concern in conventional pyrolysis processes that utilize higher value feedstocks, e.g., $C_2$-$C_4$ hydrocarbons.

There is a need, therefore, for improved pyrolysis processes, e.g., steam cracking, for upgrading a hydrocarbon feed that includes one or more contaminant-containing compositions and/or produces one or more contaminant-containing compositions during pyrolysis thereof.

SUMMARY

Processes for upgrading a hydrocarbon are provided. In some examples, The process can include determining an amount of methanol that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof. The process can also include introducing a sufficient amount of a first sorbent into a first methanol sorbent unit to allow the first methanol sorbent unit to process a depropanizer overhead that is to be separated from the steam cracker effluent for at least as long as a predetermined period of time without requiring replacement or re-activation of the first sorbent due to saturation caused by methanol present in the depropanizer overhead.

In some examples, a process for upgrading a hydrocarbon can include steam cracking a hydrocarbon feed that includes methanol to produce a steam cracker effluent that can include cracked hydrocarbons and methanol. A process gas and a naphtha cut can be separated from the steam cracker effluent. The process gas can include ethylene, propylene, and ≤40 wt. % of the methanol in the steam cracker effluent. The naphtha cut can include ≥60 wt. % of the methanol in the steam cracker effluent. A pygas product and an aqueous mixture can be separated from the naphtha cut. The aqueous mixture can include ≥95 wt. % of the methanol in the naphtha cut. The aqueous mixture can be contacted with steam to produce a vapor phase product that can include ≥80 wt. % of the methanol in the aqueous mixture and a liquid phase product that can include ≤20 wt. % of the methanol in the aqueous mixture. At least a portion of the vapor phase product can be cooled to produce a first process water. The first process water can include ≥50 wt. % (e.g., ≥60 wt. %, ≥70 wt. %, ≥80 wt. %) of the methanol contained in the steam cracker effluent.

In some examples, the process for upgrading a hydrocarbon can include steam cracking a hydrocarbon feed to produce a steam cracker effluent that can include acetone. A tar product, a steam cracker quench oil product, and an overhead can be separated from the steam cracker effluent. A process gas and a naphtha cut can be separated from the overhead. The process gas can include a first portion of the acetone, $C_2$ hydrocarbons, $C_3$ hydrocarbons, $C_4$ hydrocarbons, and $C_5$ hydrocarbons. The naphtha cut can include a second portion of the acetone, pygas, and water. The process gas can be contacted with an aqueous amine, an aqueous inorganic base, or an aqueous amine and an aqueous inorganic base to produce a first process water that can include a third portion of the acetone and an upgraded process gas that can include a fourth portion of the acetone. The amount of the third portion of acetone in the first process water can be greater than the amount of the fourth portion of acetone in the upgraded process gas. A depropanizer bottoms can be separated from the upgraded process gas. The depropanizer bottoms can include the fourth portion of acetone, the $C_4$ hydrocarbons, and the $C_5$ hydrocarbons. The depropanizer bottoms can be introduced into a debutanizer. A debutanizer overhead that can include the $C_4$ hydrocarbons and a debutanizer bottoms that can include the $C_5$ hydrocarbons can be recovered from the debutanizer. The process conditions within the debutanizer can be controlled to cause ≥60 wt. % of the acetone in the depropanizer bottoms to exit the debutanizer with the debutanizer bottoms. The debutanizer bottoms can be hydroprocessed to produce a hydrogenated product.

In some examples, the process for upgrading a hydrocarbon can include determining an amount of phenol that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof. The hydrocarbon feed can be steam cracked to produce a steam cracker effluent. A tar product, a steam cracker quench oil product, and an overhead can be separated from the steam cracker effluent. A process gas and a naphtha cut can be separated from the overhead. The naphtha cut can include a pygas, water, and phenol. A pygas product and an aqueous mixture that can include the phenol can be separated from the naphtha cut. The aqueous mixture can be contacted with a predetermined amount of a dispersant to produce a treated aqueous mixture. The predetermined amount of dispersant can be sufficient to maintain the aqueous mixture in the form of a solution that includes the phenol.

In some examples, the process for upgrading a hydrocarbon can include steam cracking a hydrocarbon feed that can include phenol to produce a steam cracker effluent that can include cracked hydrocarbons and phenol. A tar product, a steam cracker quench oil product, and an overhead can be separated from the steam cracker effluent. A process gas and a naphtha cut can be separated from the overhead. The process gas can include ethylene, propylene, and ≤3 wt. % of the phenol in the steam cracker effluent. The naphtha cut can include pygas, water, and ≥97 wt. % of the phenol in the steam cracker effluent. A pygas product and an aqueous mixture can be separated from the naphtha cut. The pygas product can include ≤40 of the phenol in the naphtha cut. The aqueous mixture can include ≥60 wt. % of the phenol in the naphtha cut. The aqueous mixture can be contacted with steam and a predetermined amount of an additive to produce a vapor phase product that can include about 5 wt. % to about 15 wt. % of the phenol in the aqueous mixture and a liquid phase product that can include about 85 wt. % to about 95 wt. % of the phenol in the aqueous mixture. The predetermined amount of additive can be sufficient to break any emulsion formed in the aqueous mixture during contact with the steam. At least a portion of the vapor phase product can be cooled to produce a first process water that can include about 4 wt. % to about 8 wt. % of the phenol contained in the steam cracker effluent. The liquid phase product can be heated to produce dilution steam. A second process water can be separated from the dilution steam. The second process water can include about 55 wt. % to about 62 wt. % of the phenol contained in the steam cracker effluent.

In some examples, the process for upgrading a hydrocarbon can include determining an amount of acetaldehyde that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof. An amount of polymer that will be produced within an amine unit and/or a caustic unit by acetaldehyde polymerizing therein can be determined, based at least in part on the determined amount of acetaldehyde that will be present in the steam cracker effluent. The hydrocarbon feed can be steam cracked to produce a steam cracker effluent that can include acetaldehyde. A tar product, a steam cracker quench oil product, and a first overhead can be separated from the steam cracker effluent. A process gas and a naphtha cut can be separated from the first overhead. The process gas can include a first portion of the acetaldehyde, ethylene, propylene, $C_4$ hydrocarbons, and $C_5$ hydrocarbons. The naphtha cut can include a second portion of the acetaldehyde, pygas, and water. The process gas can be introduced into an amine unit. The process gas can be contacted with an aqueous amine solution within the amine unit. In some examples, the process can include introducing a solvent into the amine unit at a predetermined flow rate. The solvent can be capable of dissolving the determined amount of polymer that will be produced within the amine unit. The predetermined flow rate can be sufficient to dissolve a sufficient amount of the polymer before the polymer causes fouling within the amine unit. In other examples, the process can include introducing a predetermined amount of a scavenger into the amine unit and/or caustic unit. The scavenger can limit polymerization of acetaldehyde within the amine unit and/or caustic unit to below a predetermined amount of polymer. The predetermined amount of polymer can allow the amine unit to operate without fouling due to any polymer formed from the acetaldehyde. In still other examples, the process can include introducing a rich amine purge from the amine unit into a hydroclone and/or an oil/amine separation drum having a predetermined size. The predetermined size of the hydroclone can be sufficient to remove the determined amount of polymer from the rich amine. In other examples, the process can include introducing the solvent into the amine unit, introducing the scavenger into the amine unit, and/or introducing the rich amine purge from the amine unit into the hydroclone having the predetermined size.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
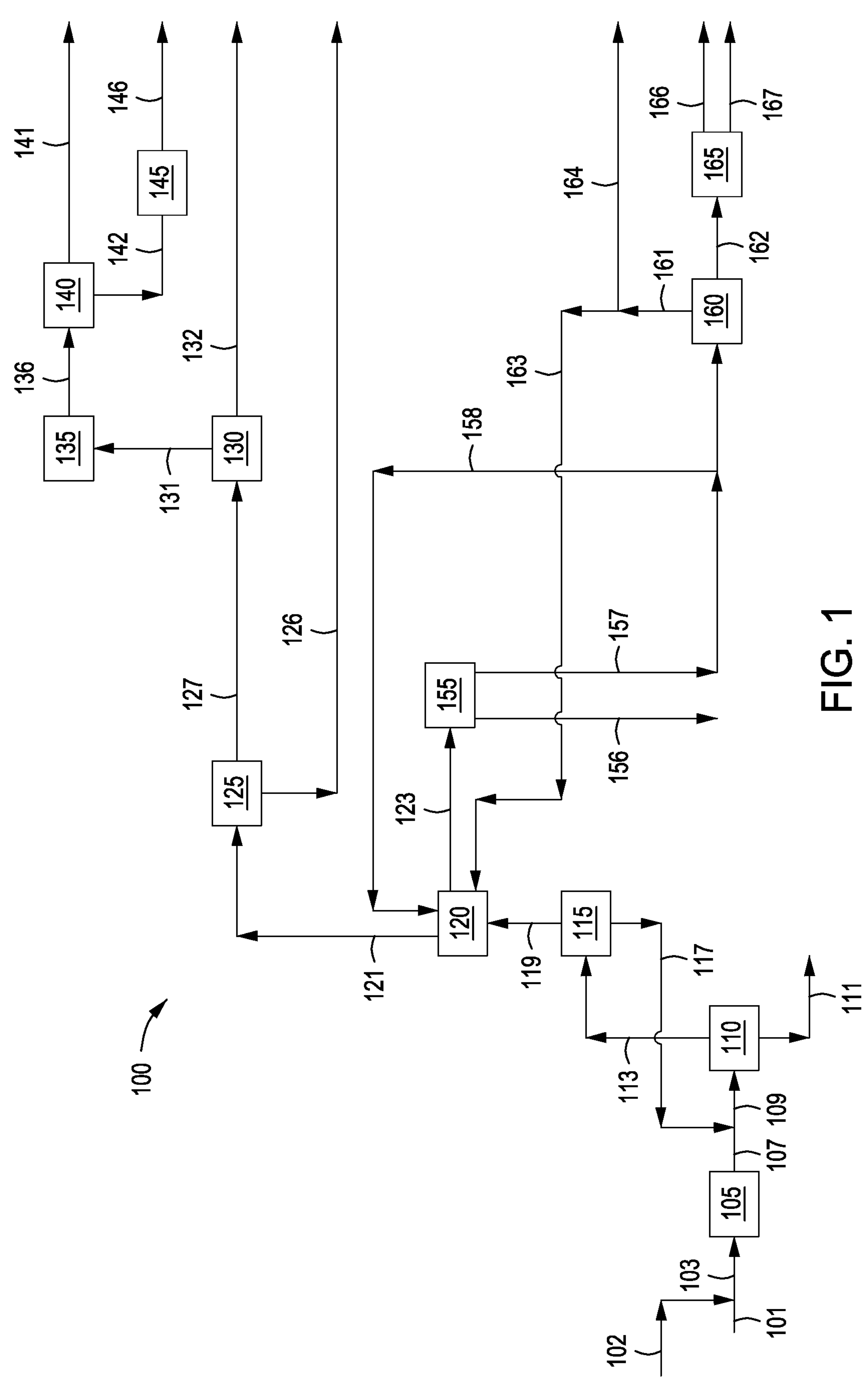
FIG. 1 depicts a schematic of an illustrative system for steam cracking a hydrocarbon feed to produce a steam cracker effluent and accounting for or otherwise handling methanol contained therein, according to one or more embodiments described.

It is to be understood that the following disclosure describes several exemplary embodiments for implementing different features, structures, and/or functions of the invention. Exemplary embodiments of components, arrangements, and configurations are described below to simplify the present disclosure: however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

It has been discovered that a pyrolysis effluent produced by pyrolyzing a hydrocarbon feed, e.g., crude oil or a fraction thereof, can include a number of contaminant-containing compositions that can cause process disruptions, e.g., saturation of a sorbent and/or fouling, and even lead to a shutdown of the pyrolysis system. For simplicity and ease of description the pyrolysis system and effluent will be further discussed and described herein in the context of a steam cracker process and plant that produces a steam cracker effluent that includes cracked hydrocarbons and one or more contaminant-containing compositions.

The contaminant-containing composition can be or can include one or more compounds that include oxygen. The contaminant-containing composition can be or can include, but is not limited to, methanol, acetone, phenol, acetaldehyde, or a mixture thereof. It has also been discovered that the amount of the contaminant-containing composition that will be present in the steam cracker effluent can be determined based, at least in part, on a composition of a hydrocarbon feed to be steam cracked, a temperature the hydrocarbon feed will be heated at during steam cracking, a residence time of the hydrocarbon feed will be heated at the temperature during steam cracking, or any combination thereof.

"Hydrocarbon" means a class of compounds containing hydrogen bound to carbon. The term "$C_n$" hydrocarbon means hydrocarbon having n carbon atom(s) per molecule, where n is a positive integer. The term "$C_{n+}$" hydrocarbon means hydrocarbon having at least n carbon atom(s) per molecule, where n is a positive integer. The term "$C_{n-}$" hydrocarbon means hydrocarbon having no more than n number of carbon atom(s) per molecule, where n is a positive integer. "Hydrocarbon" encompasses (i) saturated hydrocarbon, (ii) unsaturated hydrocarbon, and (iii) mixtures of hydrocarbons, including mixtures of hydrocarbon compounds (saturated and/or unsaturated), including mixtures of hydrocarbon compounds having different values of n. "Hydrocarbon feed" means an input into a pyrolysis process that includes hydrocarbon.

The hydrocarbon feed can include one or more of the contaminant-containing compositions and/or one or more of the contaminant-containing compositions can be produced during steam cracking of the hydrocarbon feed. It has been discovered that steam cracking the hydrocarbon feed can produce ≥0.4 ppmw, ≥0.6 ppmw, ≥0.8 ppmw, ≥1 ppmw, ≥5 ppmw, ≥8 ppmw, ≥10 ppmw, ≥30 ppmw, ≥50 ppmw, ≥80 ppmw, ≥100 ppmw, ≥120 ppmw, ≥150 ppmw, ≥180 ppmw, ≥200 ppmw, to about 250 ppmw of methanol, ≥5 ppmw, ≥8 ppmw, ≥12 ppmw, ≥20 ppmw, ≥50 ppmw, ≥80 ppmw, ≥120 ppmw, ≥150 ppmw, ≥180 ppmw, ≥200 ppmw, to about 250 ppmw of acetone, ≥1 ppmw, ≥4 ppmw, ≥6 ppmw, ≥8 ppmw, ≥10 ppmw, ≥30 ppmw, ≥50 ppmw, ≥80 ppmw, ≥100 ppmw, ≥120 ppmw, ≥150 ppmw, ≥180 ppmw, ≥200 ppmw, to about 250 ppmw of phenol, ≥1 ppmw, ≥5 ppmw, ≥8 ppmw, ≥10 ppmw, ≥30 ppmw, ≥50 ppmw, ≥80 ppmw, ≥100 ppmw, ≥120 ppmw, ≥150 ppmw, ≥180 ppmw, ≥200 ppmw, to about 250 ppmw of acetaldehyde. In some examples, the hydrocarbon feed may become contaminated with a given contaminant-containing composition, e.g., methanol, during production of the hydrocarbon feed, e.g., by injection at the wellbore, during shipping or transport of the hydrocarbon feed, and/or other source(s). Steam cracking the hydrocarbon feed that includes one or more of the contaminant-containing compositions can also decompose at least a portion of one or more of the contaminant-containing compositions.

It has been discovered that the steam cracker effluent produced by steam cracking the hydrocarbon feed, e.g., crude oil or a fraction thereof, contains about 5 wt. % to about 15 wt. % or about 8 wt. % to about 12 wt. %, e.g., about 10 wt. %, of any methanol and about 65 wt. % to about 75 wt. % or about 68 wt. % to about 72 wt. %, e.g., about 70 wt. %, of any phenol present in the heavy hydrocarbon feed and that these contaminant-containing compositions remain or at least substantially remain, e.g., ≥90 wt. %, in an overhead separated therefrom, which is further described below. The hydrocarbon feed typically does not contain acetone or acetaldehyde, but these contaminant-containing compositions are produced during steam cracking of the hydrocarbon feed. It has also been discovered that the acetone and acetaldehyde remain or at least substantially remain, e.g., ≥90 wt. %, in the overhead separated from the steam cracker effluent, which is further described below.

The composition of the hydrocarbon feed can be determined using one or more of a number of standardized tests that measure a compositional property or other property of the hydrocarbon feed. In some examples, the composition of the hydrocarbon feed can be determined by determining a total acid number (TAN), e.g., ASTM D664-18e2; a heptane insoluble asphaltene content, e.g., ASTM D6560-17; a carbon, hydrogen, and nitrogen content, e.g., ASTM D5291-16; a carbon residue, e.g., ASTM D4530-15 and/or ASTM D524-15; a density, a relative density, and/or API gravity, e.g., ASTM D4052-18a; distillation fractions, e.g., ASTM D2892-18a and/or ASTM D5236-18a; speciation and quantification of light hydrocarbons and cut point intervals in the hydrocarbon feed, e.g., ASTM D8003-15a; an amount of dissolved hydrogen sulfide, e.g., ASTM D7621-16; an amount of basic organic nitrogen, e.g., UOP269-10; an amount of phosphorus, e.g., ASTM D7111-16, ASTM D5185-18, ASTM D7691-16; a pour point, e.g., ASTM D5853-17a; an amount of salt, e.g., ASTM D3230-13(2018) and/or ASTM D6470-99(2015); total sediment particulates, e.g., ASTM D4007-11(2016)e1 and/or ASTM D4807-05 (2015); an amount of mercaptan sulfur, e.g., ASTM D3227-16 and/or UOP163-10; a total amount of sulfur, e.g., ASTM D4294-16e1; an amount of trace metals, e.g., ASTM D5708-15, ASTM D5863-00a(2016), and/or ASTM D7691-16; a UOP K factor, e.g., UOP375-07; a vapor pressure, e.g., ASTM D323-15a and/or ASTM D6377-16; a viscosity, e.g., ASTM D445-18, ASTM D446-12(2017), and/or ASTM D7042-16e3; an amount of water, e.g., ASTM D4377-00 (2011) and/or ASTM D4928-12(2018); an amount of wax, e.g., UOP46-85; or any combination thereof.

In some examples, depending on the particular contaminant-containing composition at issue, one or more steps can be taken to allow the steam cracking process to run for a predetermined period of time before requiring shutdown due to a particular contaminant-containing composition contained in the hydrocarbon feed and/or produced during steam cracking of the hydrocarbon feed. In some examples, the predetermined step(s) can include, but are not limited to, introducing a sufficient amount of a sorbent, a catalyst, or other component into one or more process stages, e.g., separation stages or reactor stages, separating a certain contaminant-containing composition from the process at one or more predetermined locations, adjusting or otherwise controlling process conditions within one or more process stages to cause a certain amount of a contaminant-containing composition to exit therefrom with a desired product, contacting one or more process effluents with a predetermined amount of one or more dispersants, one or more additives, one or more solvents, one or more scavengers, or any combination thereof, and/or installing one or more separation stages having a predetermined size configured to separate out a predetermined amount of a contaminant-containing composition or a product derived therefrom from a particular process steam.

The predetermined period of time the steam cracking process can be configured to run for can be any desired length of time. In some examples, the predetermined period of time can be about 1 day, about 2 days, about 3 days, about 5 days, about 10 days, about 15 days, about 20 days, to about 1 month, about 6 months, about 1 year, about 1.5 years, about 2 years, about 3 years, or about 4 years. In some examples, the predetermined period of time can be based, at least in part, on a desired volume of the hydrocarbon feed that is to be steam cracked during the predetermined period of time.

The hydrocarbon feed, e.g., a $C_{5+}$ hydrocarbon, can be mixed, blended, combined, or otherwise contacted with water, steam, or a mixture thereof and heated, e.g., to a temperature of about 200° C., to about 585° C., to produce a heated mixture. For example, the hydrocarbon feed can be heated by indirect heat exchange within a convection section of a steam cracker.

Hydrocarbon feeds that can be mixed, blended, combined, or otherwise contacted with the water and/or steam and heated to produce the heated mixture can be or can include, but are not limited to, raw crude oil, desalted crude oil, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, atmospheric pipestill bottoms, vacuum pipestill streams such as vacuum pipestill bottoms and wide boiling range vacuum pipestill naphtha to gas oil condensates, heavy non-virgin hydrocarbons from refineries, vacuum gas oils, heavy gas oil, naphtha contaminated with crude, atmospheric residue, heavy residue, a C4/residue admixture, naphtha/residue admixture, hydrocarbon gases/residue admixture, hydrogen/residue admixtures, waxy residues, gas oil/residue admixture, fractions thereof, or any mixture thereof. In other examples, the hydrocarbon feed can be or include, naphtha, gas oil, vacuum gas oil, waxy residues, atmospheric residues, residue admixtures, crude oil, or any mixture thereof. In some examples, a crude oil fraction can be produced by separating atmospheric pipestill ("APS") bottoms from a crude oil followed by vacuum pipestill ("VPS") treatment of the APS bottoms. In some examples, the hydrocarbon feed can be or include a crude oil such as a high-sulfur virgin crude oil rich in polycyclic aromatics or a fraction thereof. In other examples, the hydrocarbon feed can be or include a hydroprocessed hydrocarbon, e.g., a crude or resid-containing fraction thereof. In other examples, the hydrocarbon feed can be or include a vapor phase separated from a vacuum resid subjected to a thermal conversion process in a thermal conversion reactor, e.g., a delayed coker, a fluid coker, a flex-coker, a visbreaker, and/or a catalytic hydrovisbreaker). In still other examples, the hydrocarbon feed can be can include hydrocarbons having a high total acid number ("TAN"), e.g., a TAN of ≥0.5, ≥1, ≥1.5, or ≥2, as determined according to ASTM D664-18e2. In at least some examples, the hydrocarbon feed can be or can include, but is not limited to, naphtha, gas oil, vacuum gas oil, a waxy residue, an atmospheric residue, a crude oil, a fraction thereof, or a mixture thereof. In some examples, the hydrocarbon feed that can be mixed, blended, combined, or otherwise contacted with the water and/or steam and heated to produce the heated mixture can be or include the hydrocarbons or hydrocarbon feeds disclosed in U.S. Pat. Nos. 7,993,435; 8,277,639; 8,696,888; 9,327,260; 9,637,694; 9,657,239; and 9,777,227; and International Patent Application Publication No. WO 2018/111574.

In some examples, if a raw crude oil or other hydrocarbon that includes salts will be steam cracked, the raw crude oil or other hydrocarbon can optionally be subjected to pretreatment, e.g., desalting, to remove at least a portion of any salts contained in the raw crude oil or other hydrocarbon before heating the hydrocarbon feed to produce the heated mixture. In some examples, the hydrocarbon feed can be or can include a desalted crude oil derived from a raw crude oil that includes methanol, phenol, or a mixture thereof, and the desalted crude oil can include about 60 wt. % to about 80 wt. % of any methanol and/or about 60 wt. % to about 80 wt. % of any phenol present in the raw crude oil.

The heated mixture can be subjected to steam cracking conditions to produce a steam cracker effluent. In some examples, a vapor phase product or first vapor phase product and a liquid phase product or first liquid phase product can be separated from the heated mixture before subjecting the heated mixture to steam cracking by introducing the heated mixture into one or more hydrocarbon feed separation stages. The vapor phase product can be heated to a temperature of ≥400° C., e.g., a temperature of about 425° C., to about 825° C., and subjected to steam cracking conditions to produce the steam cracker effluent. In some examples, the optional hydrocarbon feed separation stage can be or include the separators and/or other equipment disclosed in U.S. Pat. Nos. 7,138,047; 7,090,765; 7,097,758; 7,820,035; 7,311,746; 7,220,887; 7,244,871; 7,247,765; 7,351,872; 7,297,833; 7,488,459; 7,312,371; 6,632,351; 7,578,929; 7,235,705; and 8,158,840.

The steam cracking conditions can include, but are not limited to, one or more of: exposing the hydrocarbon feed to a temperature (as measured at a radiant outlet of a steam cracking apparatus) of ≥400° C., e.g., a temperature of about 700° C., about 800° C., or about 900° C., to about 950° C., about 1,000° C., or about 1050° C., a pressure of about 0.1 bar to about 5 bars (absolute), and/or a steam cracking residence time of about 0.01 seconds to about 5 seconds. In some examples, the hydrocarbon feed can be steam cracked according to the processes and systems disclosed in U.S. Pat. Nos. 6,419,885; 7,993,435; 9,637,694; and 9,777,227; U.S. Patent Application Publication No. 2018/0170832; and International Patent Application Publication No. WO 2018/111574.

The steam cracker effluent can be at a temperature of ≥300° C., ≥400° C., ≥500° C., ≥600° C., or ≥700° C., or ≥800° C., or more. The steam cracker effluent can be cooled to produce a cooled steam cracker effluent. For example, the steam cracker effluent can be directly contacted with an optional quench fluid and/or indirectly cooled via one or more heat exchangers, e.g., a transfer line exchanger ("TLE"), to produce the cooled steam cracker effluent.

Those skilled in the art will appreciate that the amount of the optional quench fluid contacted with the steam cracker effluent should be sufficient to cool the steam cracker effluent to facilitate separation of desired products therefrom. In some examples, the steam cracker effluent can be cooled to a temperature of ≤300° C., e.g., about 160° C., to about 250° C., which can minimize or reduce fouling within one or more separation or other process equipment due to reactive compounds in the steam cracker effluent. Although the amount of quench fluid needed to do this can vary considerably from facility to facility, the quench fluid to steam cracker effluent weight ratio is typically in the range of from about 0.1 to about 10, e.g., 0.5 to 5, such as 1 to 4. The desired weight ratio in a particular instance can be determined, e.g., from any one or more of a number of factors such as the amount of steam cracker effluent to be cooled, the temperature of the steam cracker effluent at the quenching location, the composition and thermodynamic properties (e.g., enthalpy, $C_P$, etc.) of the quench fluid and the steam cracker effluent, the desired temperature of the quench fluid-steam cracker effluent mixture (namely the cooled steam cracker effluent) at the primary fractionator inlet, etc. For example, the cooled steam cracker effluent can include the quench fluid in an amount of about 5 wt. % to about 95 wt. %, about 25 wt. % to about 90 wt. %, or about 50 wt. %, or about 80 wt. %, based on the weight of the cooled steam cracker effluent, i.e., the combined weight of the steam cracker effluent and the quench fluid.

In some examples, a steam cracker quench oil product separated from the steam cracker effluent can be recycled and contacted with the steam cracker effluent to produce the cooled steam cracker effluent. In some examples, in lieu of or in addition to using the steam cracker quench oil product to cool the steam cracker effluent, a steam cracker gas oil product and/or one or more utility fluid products can be used. Suitable utility fluid products can include those disclosed in U.S. Pat. Nos. 9,090,836; 9,637,694, and 9,777,227, and International Patent Application Publication No. WO 2018/111574.

Those skilled in the art will also appreciate that the amount of any contaminant-containing composition, i.e., methanol, acetone, phenol, and/or acetaldehyde contained in the quench fluid, if used, should be taken into account in determining the amount of contaminant-containing composition contained in the cooled steam cracker effluent. For example, if a pygas product were used as a quench fluid, the pygas product may include at least a portion of one or more of the contaminant-containing compositions contained in the steam cracker effluent, as discussed in more detail below.

The cooled steam cracker effluent can be introduced into one or more first separation stages, e.g., a tar knock out drum, to separate a tar product and a tar-separated overhead fraction therefrom. In some examples, illustrative first separation stages can include those disclosed in U.S. Pat. No. 7,674,366; 7,718,049; 8,083,931; 8,092,671; 8,105,479.

The tar-separated overhead fraction can be at a temperature of about 155° C., about 175° C., about 200° C., or about 225° C., to a about 250° C., about 270° C., about 290° C., about 300° C., or about 315° C. The tar product can be or can include, but is not limited to, a mixture of hydrocarbons having one or more aromatic components and, optionally, non-aromatic and/or non-hydrocarbon molecules, the mixture being derived from hydrocarbon pyrolysis, with at least 70% to about 100% of the mixture having a boiling point at atmospheric pressure that is at least 290° C., e.g., 290° C., to about 500° C. In some examples, the tar product can have an initial boiling point of at least 200° C., and/or a final atmospheric boiling point of >600° C., as measured according to ASTM D2887-18. In other examples, at least 90 wt. % to about 100 wt. % of the tar product can have a boiling point at atmospheric pressure at least 290° C., e.g., 290° C., to about 500° C. In some examples, the tar product that can be separated from the steam cracker effluent and processes for upgrading same can include those described in U.S. Patent Application Publication Nos.: 2010/00096296; 2015/0344785; 2015/0344790; 2016/0122667; 2018/0057759; 2018/0171239; 2019/0016969; and 2019/0016975.

The tar-separated overhead fraction can be introduced into one or more second separation stages, e.g., a primary fractionator, to separate a steam cracker quench oil product, a steam cracker gas oil product, and the overhead therefrom. Steam cracker gas oil and steam cracker quench oil each include a mixture of compounds, primarily a mixture of hydrocarbon compounds. In some examples, at least a portion of the steam cracker quench oil product can be mixed, blended, combined, or otherwise contacted with the steam cracker effluent to produce the cooled steam cracker effluent. It should be understood that typically there is an overlap between pygas and steam cracker gas oil in composition and boiling point range. The final atmospheric boiling point of steam cracker gas oil is typically about 275° C., to about 285° C., as measured according to ASTM D2887-18. It should also be understood that typically there is an overlap between steam cracker gas oil and steam cracker quench oil in composition and boiling point range. The final atmospheric boiling point of steam cracker quench oil is typically about 455° C., to about 475° C., as measured according to ASTM D2887-18.

The overhead can include a process gas and pygas that can be introduced into one or more quench stages, e.g., a quench tower, and contacted with a quench medium, e.g., water or a recycled water, to cool the overhead and condense a mixture that includes water and pygas. The process gas and a naphtha cut can be recovered from the quench stage. The process gas can include, but is not limited to, hydrogen, methane, $C_2$ hydrocarbons, $C_3$ hydrocarbons, $C_4$ hydrocarbons, $C_5$ hydrocarbons, methanol, acetone, phenol, acetaldehyde, or any mixture thereof. The naphtha cut can include pygas, water, methanol, acetone, phenol, acetaldehyde, or any mixture thereof. Pygas, also referred to as steam cracker naphtha, is a complex mixture of $C_{5+}$ hydrocarbons, e.g., $C_5$-$C_{10+}$ hydrocarbons, having an initial atmospheric boiling point of about 25° C., to about 50° C., and a final boiling point of about 220° C., to about 265° C., as measured according to ASTM D2887-18. In some examples, pygas can have an initial atmospheric boiling point of about 33° C., to about 43° C., and a final atmospheric boiling point of about 234° C. to about 244° C., as measured according to ASTM D2887-18.

It should be understood that the first separation stage and the second separation stage, the second separation stage and the quench stage, or the first separation stage, the second separation stage, and the quench stage can be integrated with one another e.g., a single separation tower or column. In some examples, illustrative integrated separation stages can include those disclosed in U.S. Pat. Nos. 7,560,019; 8,105,479; and 8,197,668; and U.S. Patent Application Publication No. 2014/0357923; and 2014/0376511.

FIG. 1 depicts a schematic of an illustrative system 100 for steam cracking a hydrocarbon feed in line 101 to produce a steam cracker effluent via line 106 and accounting for or otherwise handling methanol contained therein, according to one or more embodiments. The system 100 can include one or more steam crackers 105, one or more first separation stages 110, e.g., tar knock-out drum, one or more second separation stages 115, e.g., primary fractionator, and one or more quench stages 120. The steam cracker 105 can optionally include one or more desalters (not shown) and/or one or more vapor/liquid separation stages (not shown) configured to separate a vapor phase product or first vapor phase product and a liquid phase product or first liquid phase product from a heated hydrocarbon and steam mixture. The first vapor phase product can be introduced into a radiant section of the steam cracker 105 and the first liquid phase product can be further processed and/or used as fuel oil, for example. The first separation stage 110, the second separation stage 115, and/or the quench stage 120 can be integrated with one another as described above. The system 100 can also include one or more process gas upgrading stages 125, e.g., one or more amine units and/or one or more caustic units, one or more depropanizers 130, one or more first methanol sorbent units 135, one or more demethanizers/deethanizers 140, and one or more second methanol sorbent units 145. The system 100 can also include one or more third separation stages 155, one or more sour water strippers 160, and one or more dilution steam generators 165.

Prior to introducing the hydrocarbon feed in line 101 into the steam cracker 105, an amount of methanol that will be present in the steam cracker effluent in line 107 can be determined. The amount of methanol that will be present in the steam cracker effluent can be determined based, at least in part, on a composition of the hydrocarbon feed in line 101, a temperature the hydrocarbon feed will be heated at during steam cracking within the steam cracker 105, a residence time the hydrocarbon feed will be heated at the temperature during steam cracking, or a combination thereof. It has been discovered that the steam cracker effluent will include about 5 wt. % to about 20 wt. % or about 8 wt. % to about 18 wt. %, e.g., about 10 wt. % to about 15 wt. %, of any methanol present in the hydrocarbon feed, i.e., the heated mixture via line 103, introduced into the steam cracker 105. It has also been discovered that and the methanol present in the steam cracker effluent in line 107 goes with an overhead separated via line 113 from the steam cracker effluent in the first separation stage 110. Accordingly, if the hydrocarbon feed contains about 70 ppmw of methanol, the steam cracker effluent will contain about 3.5 ppmw to about 14 ppmw or about 5 ppmw to about 11 ppmw, e.g., about 6 ppmw to about 8 ppmw. The methanol in the steam cracker effluent in line 107 includes any methanol contained in the hydrocarbon feed in line 101 or the heated mixture in line 103 and any methanol produced during steam cracking of the hydrocarbon feed.

In some examples, a sufficient amount of a first sorbent can be loaded or otherwise introduced into the first methanol sorbent unit 135 to allow the first methanol sorbent unit 135 to process a depropanizer overhead in line 131 that is to be separated from the steam cracker effluent in line 107 for at least as long as the predetermined period of time without requiring replacement or re-activation of the first sorbent due to saturation caused by methanol present in the depropanizer overhead to produce a first treated depropanizer overhead via line 136. In other examples, a sufficient amount of a second sorbent can be loaded or otherwise introduced into the second methanol sorbent unit 145 to allow the second methanol sorbent unit 145 to process a deethanizer bottoms in line 142 that is to be separated from the first treated depropanizer overhead in line 136 for at least as long as the predetermined period of time without requiring replacement or re-activation of the second sorbent due to saturation caused by methanol present in the deethanizer bottoms in line 142. With the amount of methanol in the steam cracker effluent and the amount, e.g., kg/hr, of steam cracker effluent that will be recovered via line 107 from the steam cracker 105, a person skilled in the art can readily determine how much of the first sorbent should be introduced into the first methanol sorbent unit 135 and how much of the second sorbent should be introduced into the second methanol sorbent unit 145.

The first sorbent and/or the second sorbent can be or include one or more adsorbent materials, absorbent materials, a mixture thereof, or a combination thereof. In some examples, the first sorbent and the second sorbent can be or can include at least one metal from Group 1, 10, or 11 of the periodic table of elements or an oxide thereof. Nomenclature of elements and groups thereof refer to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

With the first sorbent and/or the second sorbent introduced into the first methanol sorbent unit 135 and/or the second methanol sorbent unit 145, respectively, the hydrocarbon in line 101 can be mixed, blended, or otherwise combined with steam in line 102 to produce a mixture via line 103 and the mixture can be introduced into the steam cracker 105 and subjected to steam cracking conditions to produce a steam cracker effluent via line 107, as described above. The hydrocarbon feed in line 101 can be any desired hydrocarbon feed, e.g., a crude oil or a fraction thereof. In some examples, the hydrocarbon feed in line 101 can be or can include a desalted crude oil derived from a raw crude oil that includes methanol, and the desalted crude oil can include about 60 wt. % to about 80 wt. % of the methanol present in the raw crude oil. In some examples, the mixture in line 103 or a vapor phase product separated therefrom can be steam cracked according to the processes disclosed in U.S. Pat. Nos. 6,419,885; 7,993,435; 9,637,694; and 9,777,227; and International Patent Application Publication No. WO 2018/111574.

The steam cracker effluent in line 107 can be contacted with a quench fluid, e.g., a steam cracker quench oil product via line 117, to produce a cooled steam cracker effluent in line 109. The cooled steam cracker effluent in line 109 can be introduced into the first separation stage 110 and a steam cracker tar product via line 111 and a tar-separated overhead fraction via line 113 can be conducted away therefrom. The tar-separated overhead fraction via line 113 can be introduced into the second separation stage 115 and the steam cracker quench oil product via line 117 and an overhead via line 119 can be conducted away therefrom.

The overhead via line 119 can be introduced into the quench stage 120 and can be contacted with a quench medium, e.g., water recovered from a downstream process such as water via line 158 and/or 163, to produce a cooled overhead. A second overhead or process gas via line 121 and a naphtha cut via line 123 can be conducted away from the quench stage 120. The process gas in line 121 can include, but is not limited to, a first portion of the methanol and hydrogen, methane, $C_2$ hydrocarbons, $C_3$ hydrocarbons, $C_4$ hydrocarbons, $C_5$ hydrocarbons, acetone, phenol, acetaldehyde, or any mixture thereof. The naphtha cut in line 123 can include, but is not limited to, a second portion of the methanol, pygas, and quench medium, e.g., water.

It has been discovered that the process gas in line 121 can include less of the methanol contained in the steam cracker effluent in line 107 than the naphtha cut in line 123. For example, the process gas in line 121 can include about 10 wt. %, about 20 wt. %, or about 25 wt. % to about 35 wt. %, about 40 wt. %, or about 45 wt. % of the methanol contained in the steam cracker effluent in line 107, whereas the naphtha cut in line 123 can include about 55 wt. %, about 60 wt. %, or about 65, wt. % to about 75 wt. %, about 80 wt. %, or about 90 wt. % of the methanol contained in the steam cracker effluent in line 107. In some examples, the process gas in line 121 can include about 25 wt. % to about 35 wt. %, e.g., about 30 wt. % of the methanol contained in the seam cracker effluent in line 107 and the naphtha cut in line 123 can include about 65 wt. % to about 75 wt. %, e.g., about 70 wt. % of the methanol contained in the steam cracker effluent in line 107.

The process gas via line 121 can be contacted with an amine solution and/or a caustic solution via line 124 within the process gas upgrading stage 125 and at least a portion of acid gases, e.g., hydrogen sulfide, in the process gas can be transferred to the amine solution and/or the caustic solution. A process water or third process water via line 126 and a treated process gas or upgraded process gas via line 127 can be recovered from the process gas upgrading stage 125. The process gas upgrading stage 125 can also remove a majority of the methanol from the process gas as a component of the process water recovered via line 126. In some examples, the process gas upgrading unit 125 can include one or more amine towers, one or more caustic towers, or a combination thereof. In some examples, the process water recovered via line 126 can be a single process water stream or a plurality of process water streams. In some examples, if the process gas upgrading unit includes an amine tower, the rich amine solution recovered therefrom can be regenerated to produce a light amine that can be recycled to the amine tower. The upgraded process gas in line 127 can include at least a portion of the methanol contained in the seam cracker effluent in line 107. For example, the amount of the methanol from the steam cracker effluent in line 107 present in the upgraded process gas in line 127 can be >0 wt. % and <1 wt. %, <0.5 wt. %, <0.5 wt. %, <0.3 wt. %, <0.1 wt. %, <0.08 wt. %, <0.06 wt. %, <0.04 wt. %, <0.03 wt. %, <0.02 wt. %, <0.01 wt. %, <0.007 wt. %, <0.005 wt. %, <0.003 wt. %, <0.001 wt. %, <0.0007 wt. %, <0.0005 wt. %, or <0.0003 wt. %.

The upgraded process gas via line 127 can be introduced into the depropanizer 130 and a depropanizer overhead via line 131 and a depropanizer bottoms via line 132 can be conducted away therefrom. The depropanizer overhead via line 131 can be introduced into the first methanol sorbent unit 135 and can be contacted therein with the first sorbent for at least the predetermined period of time without requiring replacement or re-activation of the first sorbent due to saturation caused by methanol present in the depropanizer overhead and a treated depropanizer overhead via line 136 can be conducted away therefrom. During contact between the depropanizer overhead and the first methanol sorbent, the first methanol sorbent can remove at least a portion of the methanol present in the depropanizer overhead and the treated depropanizer overhead can be recovered via line 136. For example, the first methanol sorbent can adsorb at least a portion of the methanol present in the depropanizer overhead to produce the treated depropanizer overhead. As such, the treated depropanizer overhead in line 136 can include less methanol than the depropanizer overhead in line 131. In some examples, the treated depropanizer overhead in line 136 can include methanol, but the amount of methanol present in the treated depropanizer overhead in line 136 can be, e.g., less than about 50 wt. % of the methanol present in the depropanizer overhead in line 131.

The treated depropanizer overhead via line 136 can be introduced to the demethanizer/deethanizer 140 to produce a deethanizer overhead via line 141 and a deethanizer bottoms via line 142. The demethanizer and deethanizer are shown as a single unit, however, the demethanizer and deethanizer can be separate units and any number of demethanizers and/or deethanizers can be used to produce the deethanizer overhead via lien 141 and the deethanizer bottoms via line 142. The deethanizer overhead in line 141 can include hydrogen, methane, ethane, ethylene, or any mixture thereof. The deethanizer bottoms in line 142 can include propane, propylene, and any methanol that may have not been removed within the first methanol sorbent unit 135.

The deethanizer bottoms via line 142 can be introduced to the second methanol sorbent unit 145 and contacted therein with the second sorbent for at least the predetermined period of time without requiring replacement or re-activation of the second sorbent due to saturation caused by methanol present in the deethanizer bottoms and a treated deethanizer product via line 146 can be conducted away therefrom. The treated deethanizer bottoms in line 146 can include propane, propylene, and be free of any methanol or include <0.01 wt. %, less than 0.005 wt. %, less than 0.001 wt. %, less than 0.0005 wt. %, or less than 0.0001 wt. % of the methanol present in the steam cracker effluent in line 107.

Returning to the naphtha cut in line 123, the effluent via line 123 can be introduced into the third separation stage 155 to produce a pygas product via line 156 and an aqueous mixture via line 157 that can include methanol, e.g., ≥95 wt. % of the methanol present in the effluent in line 123. The aqueous mixture via line 157 can be introduced into the sour water stripper 160 to produce a sour water stripper overhead or second vapor phase product via line 161 and a sour water stripper bottoms or a second liquid phase product via line 162.

In some examples, the aqueous mixture can be contacted with steam, e.g., counter currently, within the sour water stripper 160, to produce the second vapor phase product that can be recovered via line 161. Contacting the aqueous mixture with the steam can cause a majority, i.e., >50 wt. % of the methanol in the aqueous mixture to exit the sour water stripper 160 as a component of the second vapor phase product via line 161. In some examples, at least a portion of the aqueous mixture via line 157 can be recycled to the quench stage via line 158 as the quench medium or a portion of the quench medium.

In some examples, the aqueous mixture in line 123 can include >50 wt. %, ≥55 wt. %, ≥60 wt. %, ≥65 wt. %, ≥70 wt. %, ≥75 wt. %, ≥80 wt. %, or ≥85 wt. % of the methanol contained in the steam cracker effluent in line 107. In some examples, the process gas in line 121 can include <50 wt. %, ≤45 wt. %, ≤40 wt. %, ≤35 wt. %, ≤30 wt. %, ≤25 wt. %, ≤20 wt. %, or ≤15 wt. % of the methanol contained in the steam cracker effluent in line 107. In some examples, the first process water in line 164 can include >30 wt. %, ≥40 wt. %, ≥45 wt. %, ≥50 wt. %, ≥55 wt. %, ≥60 wt. %, ≥65 wt. % of the methanol contained in the steam cracker effluent in line 107. In some examples, the second process water in line 162 can include <50 wt. %, ≤45 wt. %, ≤40 wt. %, ≤35 wt. %, ≤30 wt. %, ≤25 wt. %, ≤20 wt. %, ≤15 wt. %, or ≤10 wt. % of the methanol contained in the steam cracker effluent in line 107.

In some examples, at least a portion of the second vapor phase product in line 161 can be condensed, e.g., via indirect heat exchange or direct contact with a cooling medium such as water, to produce a process water or first process water via line 164. In some examples, a portion of the second vapor phase product in line 161 can be recycled via line 163 to the quench stage 120 as at least a portion of the quench medium.

In some examples, a mass flow rate of the process water in line 164 can be about 1%, about 5%, about 10%, about 20%, about 30%, or about 40% to about 60%, about 70%, about 80%, about 90%, or about 100% of a mass flow rate of the vapor phase product or second vapor phase product in line 161. In other examples, the mass flow rate of the process water in line 164 can be about 1% to about 20%, about 3% to about 15, about 5% to about 20%, about 10% to about 35%, about 5% to about 15%, about 25% to about 50%, about 40% to about 80%, or about 50% to about 90% of the mass flow rate of the vapor phase product or second vapor phase product in line 161.

In some examples, a mass flow rate of the process water in line 164 can be about 1%, about 3%, about 5%, or about 7% to about 10%, about 12%, about 15%, about 17%, or about 20% of a mass flow rate the aqueous mixture in line 157 separated from the naphtha cut in line 123. In other examples, the mass flow rate of the process water in line 164 can be about 1% to about 20%, about 3% to about 15%, about 5% to about 10% about 4% to about 12%, or about 3% to about 15% the mass flow rate the aqueous mixture in line 157 separated from the naphtha cut in line 123.

The second liquid phase product via line 162 can be conducted away from the sour water stripper 160 and can be introduced into the dilution steam generator 165 to produce dilution steam via line 166 and a process water or second process water via line 167. The dilution steam generator 165 can heat the second liquid phase product in line 162 to produce dilution steam. The second process water via line 167 and the dilution steam via line 166 can be conducted away from the dilution steam generator 165.

In some examples, the first process water in line 164 can include ≥80 wt. %, ≥82 wt. %, or ≥85 wt. % of the methanol in the aqueous mixture in line 157 and the second process water in line 167 can include ≤20 wt. %, ≤17 wt. %, or less than 15 wt. % of the methanol in the aqueous mixture in line 157. In some examples, the second process water in line 167 can include ≥75 wt. %, ≥80 wt. %, ≥85 wt. %, ≥90 wt. %, ≥95 wt. %, or about 100 wt. % of the methanol contained in the second liquid phase product in line 162.

In some examples, the first process water in line 164 can include about 55 wt. % to about 65 wt. % of the methanol contained in the steam cracker effluent in line 107, the second process water in line 167 can include about 5 wt. % to about 15 wt. % of the methanol contained in the steam cracker effluent in line 107, and the process gas in line 121 can include about 25 wt. % to about 35 wt. % of the methanol contained in the steam cracker effluent in line 107. In other examples, the first process water in line 164 can include about 55 wt. % to about 65 wt. % of the methanol contained in the steam cracker effluent in line 107, the second process water in line 167 can include about 5 wt. % to about 15 wt. % of the methanol contained in the steam cracker effluent in line 107, the process water in line 126 can include about 25 wt. % to about 35 wt. % of the methanol contained in the steam cracker effluent in line 107, and the upgraded process gas in line 127 can include ≤5 wt. %, ≤4 wt. %, ≤3 wt. %, ≤2 wt. %, ≤1 wt. %, ≤0.5 wt. %, or ≤0.1 wt. % of the methanol contained in the steam cracker effluent in line 107.

Figure 2:
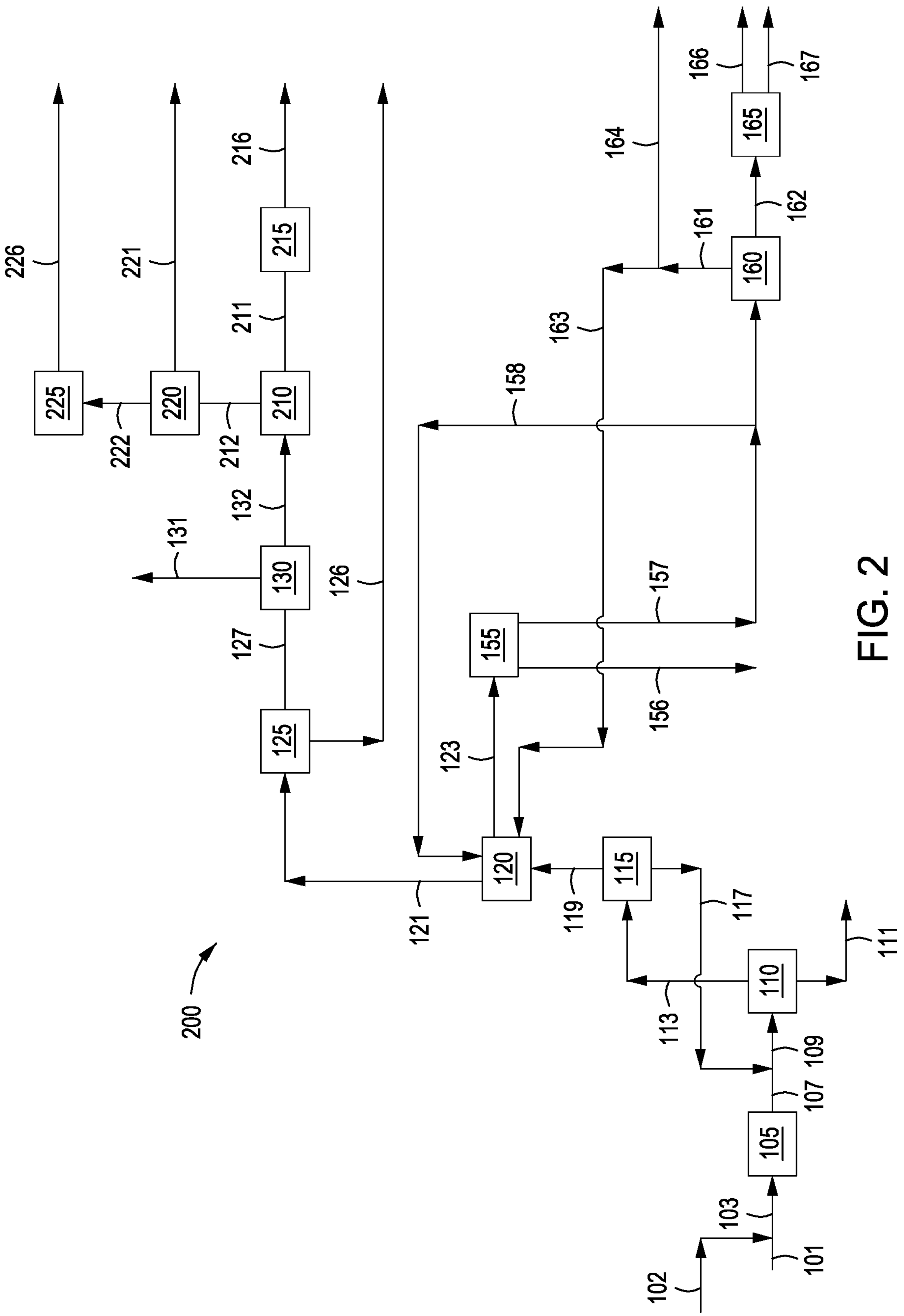
FIG. 2 depicts a schematic of an illustrative system for steam cracking a hydrocarbon feed to produce a steam cracker effluent and accounting for or otherwise handling acetone contained therein, according to one or more embodiments described.

FIG. 2 depicts a schematic of an illustrative system 200 for steam cracking a hydrocarbon feed in line 101 to produce a steam cracker effluent via line 107 and accounting for or otherwise handling acetone contained therein, according to one or more embodiments. The system 200 can include the one or more steam crackers 105, the one or more first separation stages 110, the one or more second separation stages 115, the one or more quench stages 120, the one or more process gas upgrading stages 125, the one or more depropanizers 130, the one or more third separation stages 155, the one or more sour water strippers 160, and the one or more dilution steam generators 165, as described above with reference to FIG. 1. The system 200 can also include one or more debutanizers 210, one or more $C_4$ caustic units 220, one or more butadiene extractive distillation units 225, and one or more hydroprocessing units 215.

A process gas via line 121 and a naphtha cut via line 123 can be recovered from the quench stage 120 as described above with reference to FIG. 1. The process gas in line 121 can include, but is not limited to, a first portion of the acetone and hydrogen, methane, $C_2$ hydrocarbons, $C_3$ hydrocarbons, $C_4$ hydrocarbons, $C_5$ hydrocarbons, or any mixture thereof. The naphtha cut in line 123 can include, but is not limited to, a second portion of the acetone, pygas, and quench medium, e.g., water.

The hydrocarbon feed in line 101 typically does not include acetone, which is primarily if not exclusively produced during steam cracking of the hydrocarbon feed in the steam cracker 105. It has been discovered that steam cracking the hydrocarbon feed can produce ≥5 ppmw, ≥8 ppmw, or ≥12 ppmw to about 250 ppmw of acetone. As such, the steam cracker effluent in line 107 can include acetone at a concentration from, e.g., 0.1, 0.2, 0.3, 0.4, 0.5, 0.6, 0.7, 0.8, 0.9, ppmw, to 1, 2, 3, 4, 5, 6, 7, 8, 9, ppmw, to 10, 20, 30, 40, 50, 60, 70, 80, 90, ppmw, to 120, 140, 150, 160, 180, ppmw, to 200, 210, 220, 230, 240, 250 ppmw, based on the total weight of the steam cracker effluent in line 107. Should the hydrocarbon feed be contaminated with acetone, e.g., similar to how methanol can become a component of the hydrocarbon feed, any acetone present in the hydrocarbon feed can be readily determined by determining the composition of the hydrocarbon feed in line 101.

The process gas in line 121 can include ≥35 wt. % or ≤30 wt. % of the acetone in the steam cracker effluent in line 107 and the naphtha cut in line 123 can include ≥65 wt. % or ≥70 wt. % of the acetone in line the steam cracker effluent in line 107. The process gas via line 121 can be subjected to an amine and/or caustic treatment within the process gas upgrading stage 125 to produce a process water or "first" process water via line 126 and an upgraded process gas via line 127. The first process water in line 126 can include a portion or "third portion" of the acetone and the upgraded process gas in line 127 can include a portion or "fourth portion" of the acetone. In some examples, a majority, i.e., >50 wt. %, of the acetone contained in the process gas in line 121 can be removed as a component of the first process water recovered via line 126.

The first process water in line 126 can include >50 wt. %, ≥52 wt. %, ≥54 wt. %, or ≥56 wt. % of the acetone contained in the process gas in line 121 and the upgraded process gas in line 127 can include <50 wt. %, ≤48 wt. %, ≤46 wt. %, or ≤44 wt. % of the acetone contained in the process gas in line 121. In some examples, the first process water in line 126 can include about 54 wt. % or about 56 wt. % to about 58 wt. % or about 60 wt. %, e.g., about 57 wt. %, of the acetone contained in the process gas in line 121 and the upgraded process gas in line 127 can include about 40 wt. % or about 42 wt. % to about 44 wt. % to about 46 wt. %, e.g., about 43 wt. %, of the acetone contained in the process gas in line 121.

In some examples, the first process water in line 126 can include about 13 wt. %, about 14 wt. %, or about 15 wt. % to about 18 wt. %, about 19 wt. %, or about 20 wt. % of the acetone present in the steam cracker effluent in line 107. In some examples, the upgraded process gas in line 127 can include about 10 wt. %, about 11 wt. %, or about 12 wt. % to about 14 wt. %, about 15 wt. %, or about 16 wt. % of the acetone present in the steam cracker effluent in line 107. In other examples, the process water in line 126 can include about 16 wt. % to about 18 wt. %, e.g., about 17 wt. %, of the acetone present in the steam cracker effluent in line 107 and the upgraded process gas in line 127 can include about 12 wt. % to about 14 wt. %, e.g., about 13 wt. %, of the acetone present in the steam cracker effluent in line 107.

The upgraded process gas via line 127 can be introduced into the depropanizer 130 and a depropanizer overhead via line 131 and a depropanizer bottoms via line 132 can be recovered therefrom. The depropanizer bottoms in line 132 can include all or substantially all, e.g., ≥95 wt. %, of the fourth portion of the acetone, any $C_4$ hydrocarbons, and any $C_5$ hydrocarbons present in the upgraded process gas in line 127. The depropanizer bottoms in line 132 can include, but is not limited to, the fourth portion of acetone, the $C_4$ hydrocarbons, and the $C_5$ hydrocarbons contained in the process gas in line 121.

The depropanizer bottoms via line 132 can be introduced into the debutanizer 210 and a debutanizer overhead via line 212 and a debutanizer bottoms via line 211 can be conducted away therefrom. The debutanizer overhead in line 212 can include acetone and the $C_4$ hydrocarbons and the debutanizer bottoms can include acetone and the $C_5$ hydrocarbons from the depropanizer bottoms in line 132. The $C_4$ hydrocarbons in the debutanizer overhead can include butadiene.

The debutanizer overhead via line 212 can be introduced into the $C_4$ caustic unit 220 and contacted with a caustic solution to produce a caustic treated overhead via line 222 and a water purge via line 221. For example, the debutanizer overhead in line 212 can be contacted with an aqueous sodium hydroxide solution, an aqueous potassium hydroxide solution, or any mixture thereof to produce the caustic treated overhead in line 222 and the water purge in line 221. Contacting the debutanizer overhead in line 212 with the caustic solution can produce the water purge in line 221 that can include ≥50 wt. %, ≥55 wt. %, ≥60 wt. %, ≥65 wt. %, ≥70 wt. %, or ≥75 wt. % of the acetone contained in the debutanizer overhead in line 212.

The caustic treated overhead via line 222 can be introduced into the butadiene extractive distillation unit 225 to produce $C_4$ product via line 226 that can have a reduced amount of butadiene as compared to the caustic treated overhead in line 222. In some example, at least a portion of the butadiene in the caustic treated overhead in line 222 can be removed by contacting the caustic treated overhead in line 222 with one or more extraction solvents. Illustrative extraction solvents can be or can include, but are not limited to, dimethylforamide, acetonitrile, N-methyl pyrolidone, or any mixture thereof.

It has been discovered that acetone contained in the debutanizer overhead in line 212 can cause issues during the processing of the debutanizer overhead in line 222. For example, acetone present in the debutanizer overhead in line 222 can cause fouling in downstream processes (e.g., a butadiene extraction process). Accordingly, it has also been discovered that by controlling the process conditions within the debutanizer 210 to cause a majority, e.g., ≥50 wt. %, of the acetone present in the depropanizer bottoms in line 132 to exit the debutanizer 210 with the debutanizer bottoms via line 211, the issues that can arise during processing of the debutanizer overhead in line 222, with regard to acetone being present, can be significantly reduced or eliminated.

In some examples, the process conditions within the debutanizer 210 can be controlled to lessen the amount of $C_5$ hydrocarbon in the debutanizer overhead, leading to a desirable decrease in the amount of acetone in the debutanizer overhead, such that ≥60 wt. %, ≥63 wt. %, ≥65 wt. %, ≥67 wt. %, or ≥69 wt. % of the acetone contained in the depropanizer bottoms in line 132 to exit the debutanizer 210 with the debutanizer bottoms via line 211. In some examples, the debutanizer 210 process conditions can include, but are not limited to, (i) a pressure from, e.g., 20, 22, 24, 25, 26, 28, psig, to 30, 32, 34, 35, 36, 38, 40, psig, to 42, 44, 45, 46, 48, 50, psig; and (ii) a pressure from 200, 210, 220, 230, 240, 250, ° F., to 260, 270, 280, 290, 300, ° F. In some examples, the process conditions within the debutanizer 210 can be controlled to cause about 62 wt. %, about 64 wt. %, about 66 wt. %, or about 68 wt. % to about 70 wt. %, about 72 wt. %, about 74 wt. %, or about 76 wt. % of the acetone contained in the depropanizer bottoms in line 132 to exit the debutanizer 210 with the debutanizer bottoms via line 211.

The debutanizer bottoms via line 211 can be introduced into the hydroprocessing unit 215 to produce a hydroprocessed product via line 216. In some examples, ≥80 wt. %, ≥85 wt. %, ≥90 wt. %, or ≥95 wt. % of any acetone contained in the debutanizer bottoms in line 211 can be converted into benzene and water. The debutanizer bottoms via line 211 can be hydroprocessed alone or in the presence of one or more other process effluents.

The hydroprocessing of the debutanizer bottoms in line 211 can be carried out in one or more hydroprocessing stages under hydroconversion conditions that can be independently selected for each stage, e.g., under conditions for carrying out one or more of pre-treatment, hydrocracking (including selective hydrocracking), hydrogenation, hydrotreating, hydrodesulfurization, hydrodenitrogenation, hydrodemetallation, bydrodearomatization, hydroisomerization, and/or hydrodewaxing as the case may be. In some examples, the debutanizer bottoms in line 211 can be hydroprocessed in one or more hydroprocessing units that can include one or more hydroprocessing vessels or zones. The hydroprocessing vessel or zone can include one or more catalysts disposed therein. The catalyst can be in the form of a fixed catalyst bed, a circulating or slurry bed, or any other configuration.

In some examples, the hydroprocessing conditions can include a temperature of about 40° C., about 75° C., or about 100° C., to about 200° C., about 300° C., or about 370° C. In some examples, the hydroprocessing conditions can be carried out under an absolute pressure of about 600 kPa, about 1,000 kPa, or about 1,500 kPa to about 2,000 kPa, about 2,750 kPa, or about 3,500 kPa. In some examples, the hydroprocessing conditions can be carried out at a weight hourly space velocity (WHSV) of about 1 $h^{-1}$, about 3 $h^{-1}$, or about 5 $h^{-1}$ to about 8 $h^{-1}$, about 12 $h^{-1}$, or about 15 $h^{-1}$. In at least one example, the hydroprocessing conditions can include a temperature of about 40° C., to about 370° C., an absolute pressure of about 600 kPa to about 3500 kPa, and a weight hourly space velocity (WHSV) of catalyst of from about 1 $h^{-1}$ to about 15 $h^{-1}$.

In some examples, hydroprocessing the debutanizer bottoms in line 211 can include hydroprocessing the debutanizer bottoms under a first set of hydroprocessing conditions to produce an intermediate or pre-treated debutanizer bottoms. The pre-treated debutanizer bottoms can be hydroprocessed under a second set of hydroprocessing conditions to produce the hydroprocessed product in line 216. The first set of hydroprocessing conditions and the second set of hydroprocessing conditions can be the same or different with respect to one another. In some examples, the first set of hydroprocessing conditions can be configured to selectively hydrogenate dienes to monoolefins (with some hydrodesulfurizaton optionally occurring) and the second set of hydroprocessing conditions can be configured to selectively hydrodsulfurize (with some hydrogenation optionally occurring).

In some examples, the debutanizer bottoms in line 211 can be hydroprocessed under the first set of hydroprocessing conditions in the presence of molecular hydrogen and a first catalyst to produce a pre-treated debutanizer bottoms and the pre-treated debutanizer bottoms can be hydroprocessed under the second set of hydroprocessing conditions in the presence of molecular hydrogen and a second catalyst to produce the hydroprocessed product via line 216. The first catalyst and the second catalyst can be the same or different with respect to one another. In some examples, the first catalyst can be or include nickel. For example, the first catalyst can be or include nickel sulfide. In some examples, the second catalyst can be or include nickel, molybdenum, cobalt, alloys thereof, or a mixture or combination thereof. In some examples, the second catalyst can be or include a nickel molybdenum catalyst and/or a cobalt molybdenum catalyst.

If the hydroprocessing unit 215 includes two hydroprocessing stages, the first set of hydroprocessing conditions in the first hydroprocessor can include a temperature of about 40° C., about 75° C., or about 100° C., to about 200° C., about 300° C., or about 375° C. The first set of hydroprocessing conditions in the first hydroprocessor can be carried out under an absolute pressure of about 600 kPa, about 1,000 kPa, or about 1,500 kPa to about 2,000 kPa, about 2,750 kPa, or about 3,500 kPa. The first set of hydroprocessing conditions in the first hydroprocessor can be carried out at a weight hourly space velocity (WHSV) of about 1 $h^{-1}$, about 3 $h^{-1}$, or about 5 $h^{-1}$ to about 8 $h^{-1}$, about 12 $h^{-1}$, or about 15 $h^{-1}$.

In some examples, the second set of hydroprocessing conditions in the second hydroprocessor can include a temperature of about 40° C., about 75° C., or about 100° C., to about 200° C., about 300° C., or about 375° C. The second set of hydroprocessing conditions in the second first hydroprocessor 230 can be carried out under an absolute pressure of about 600 kPa, about 1,000 kPa, or about 1,500 kPa to about 2,000 kPa, about 2,750 kPa, or about 3,500 kPa. The second set of hydroprocessing conditions in the first hydroprocessor 230 can be carried out at a weight hourly space velocity (WHSV) of about 1 $h^{-1}$, about 3 $h^{-1}$, or about 5 $h^{-1}$ to about 8 $h^{-1}$, about 12 $h^{-1}$, or about 15 $h^{-1}$. In some examples, suitable hydroprocessors and processes for operating same that can be used to hydroprocess the debutanizer bottoms in line 211 and other process streams, e.g., the pygas in line 156, can include those disclosed in U.S. Pat. Nos. 5,807,477; 5,679,241; 5,851,383; 8,163,167; 8,894,844; and U.S. Patent Application No.: 2007/0170098; and 2016/0376511.

Hydroprocessing the debutanizer bottoms can convert ≥75 wt. %, 80 wt. %, ≥85 wt. %, ≥90 wt. %, ≥95 wt. %, or ≥97.5 wt. % of the acetone to propane and water. If the hydroprocessing unit 215 includes a first hydroprocessor and a second hydroprocessor, the first hydroprocess can convert ≥40 wt. %, ≥, 45 wt. %, ≥50 wt. %, ≥55 wt. %, or ≥60 wt. % of the acetone in the debutanizer bottoms to propane and water and the second hydroprocessor can convert ≥85 wt. %, ≥90 wt. %, ≥95 wt. %, or ≥97.5 wt. % of any remaining acetone in the pre-treated debutanizer bottoms.

Returning to the naphtha cut in line 123, the naphtha cut via line 123 can be introduced into the third separation stage 155 to produce pygas via line 156 and an aqueous mixture via line 157. The pygas in in line 156 can include acetone or a "fifth portion" of the acetone and the aqueous mixture in line 157 can include acetone or a "sixth portion" of the acetone. In some examples, the pygas in line 156 can include about 70 wt. %, about 75 wt. %, or about 78 wt. % to about 82 wt. %, about 84 wt. %, or about 86 wt. % of the acetone contained in the naphtha cut in line 123. In some examples, the aqueous mixture in line 157 can include about 10 wt. %, about 15 wt. %, or about 17 wt. % to about 22 wt. %, about 25 wt. %, or about 30 wt. % of the acetone contained in the naphtha cut in line 123.

In some examples, the pygas in line 156, as noted above, can be introduced into the hydroprocessing unit 215. For example, the debutanizer bottoms in line 211 can be mixed, blended, or otherwise combined with the pygas in line 156 to produce a mixture and the mixture can be introduced into the hydroprocessing unit 215. Hydroprocessing the mixture of the debutanizer bottoms and the pygas can convert ≥75 wt. %, ≥80 wt. %, ≥85 wt. %, ≥90 wt. %, ≥95 wt. %, or ≥97.5 wt. % of the acetone in the mixture to propane and water to produce the pre-treated mixture. If the hydroprocessing unit 215 includes a first hydroprocessor and a second hydroprocessor, the first hydroprocess can convert ≥40 wt. %, ≥, 45 wt. %, ≥50 wt. %, ≥55 wt. %, or ≥60 wt. % of the acetone in the mixture to propane and water and the second hydroprocessor can convert ≥85 wt. %, ≥90 wt. %, ≥95 wt. %, or ≥97.5 wt. % of any remaining acetone in the pre-treated mixture bottoms.

The aqueous mixture via line 157 can be introduced into the sour water stripper 160 to produce a sour water stripper overhead or second vapor phase product via line 161 and a sour water stripper bottoms or a second liquid phase product via line 162. In some examples, the aqueous mixture can be contacted with steam, e.g., counter currently, within the sour water stripper 160, to produce the second vapor phase product that can be recovered via line 161. Contacting the aqueous mixture with the steam can cause a majority, i.e., >50 wt. % of the acetone in the aqueous mixture to exit the sour water stripper 160 as a component of the second vapor phase product via line 161. In some examples, at least a portion of the aqueous mixture via line 157 can be recycled to the quench stage via line 158 as the quench medium or a portion of the quench medium.

In some examples, at least a portion of the second vapor phase product in line 161 can be condensed, e.g., via indirect heat exchange or direct contact with a cooling medium such as water, to produce a process water or second process water via line 164. In some examples, a portion of the second vapor phase product in line 161 can be recycled via line 163 to the quench stage 120 as at least a portion of the quench medium.

In some examples, a mass flow rate of the process water in line 164 can be about 1%, about 5%, about 10%, about 20%, about 30%, or about 40% to about 60%, about 70%, about 80%, about 90%, or about 100% of a mass flow rate of the vapor phase product or second vapor phase product in line 161. In other examples, the mass flow rate of the process water in line 164 can be about 1% to about 20%, about 3% to about 15, about 5% to about 20%, about 10% to about 35%, about 5% to about 15%, about 25% to about 50%, about 40% to about 80%, or about 50% to about 90% of the mass flow rate of the vapor phase product or second vapor phase product in line 161.

In some examples, a mass flow rate of the process water in line 164 can be about 1%, about 3%, about 5%, or about 7% to about 10%, about 12%, about 15%, about 17%, or about 20% of a mass flow rate the aqueous mixture in line 157 separated from the naphtha cut in line 123. In other examples, the mass flow rate of the process water in line 164 can be about 1% to about 20%, about 3% to about 15%, about 5% to about 10% about 4% to about 12%, or about 3% to about 15% the mass flow rate the aqueous mixture in line 157 separated from the naphtha cut in line 123.

The second liquid phase product via line 162 can be conducted away from the sour water stripper 160 and can be introduced into the dilution steam generator 165 to produce dilution steam via line 166 and a process water or third process water via line 167. The dilution steam generator 165 can heat the second liquid phase product in line 162 to produce dilution steam. The third process water via line 167 and steam via line 166 can be conducted away from the dilution steam generator 165. In some examples, the second process water in line 164 can include ≥80 wt. %, ≥85 wt. %, ≥87 wt. %, or ≥90 wt. % of the acetone contained in the aqueous mixture in line 157 and the third process water in line 167 can include ≤20 wt. %, ≤15 wt. %, ≤12 wt. %, or less than 10 wt. % of the acetone contained in the aqueous mixture in line 157.

In some examples, the first process water in line 126 can include about 12 wt. % to about 22 wt. % of the acetone contained in the steam cracker effluent in line 107, the water purge in line 221 can include about 1 wt. % to about 6 wt. % of the acetone contained in the steam cracker effluent in line 107, the second process water in line 164 can include about 8 wt. % to about 18 wt. % of the acetone contained in the steam cracker effluent in line 107, the third process water in line 167 can include about 0.5 wt. % to about 4 wt. % of the acetone contained in the steam cracker effluent in line 107, the pygas can include about 45 wt. % to about 65 wt. % of the acetone contained in the steam cracker effluent in line 107, and the caustic treated overhead in line 222 can include ≤3 wt. %, ≤2 wt. %, or ≤1 wt. % of the acetone contained in the steam cracker effluent in line 107.

Figure 3:
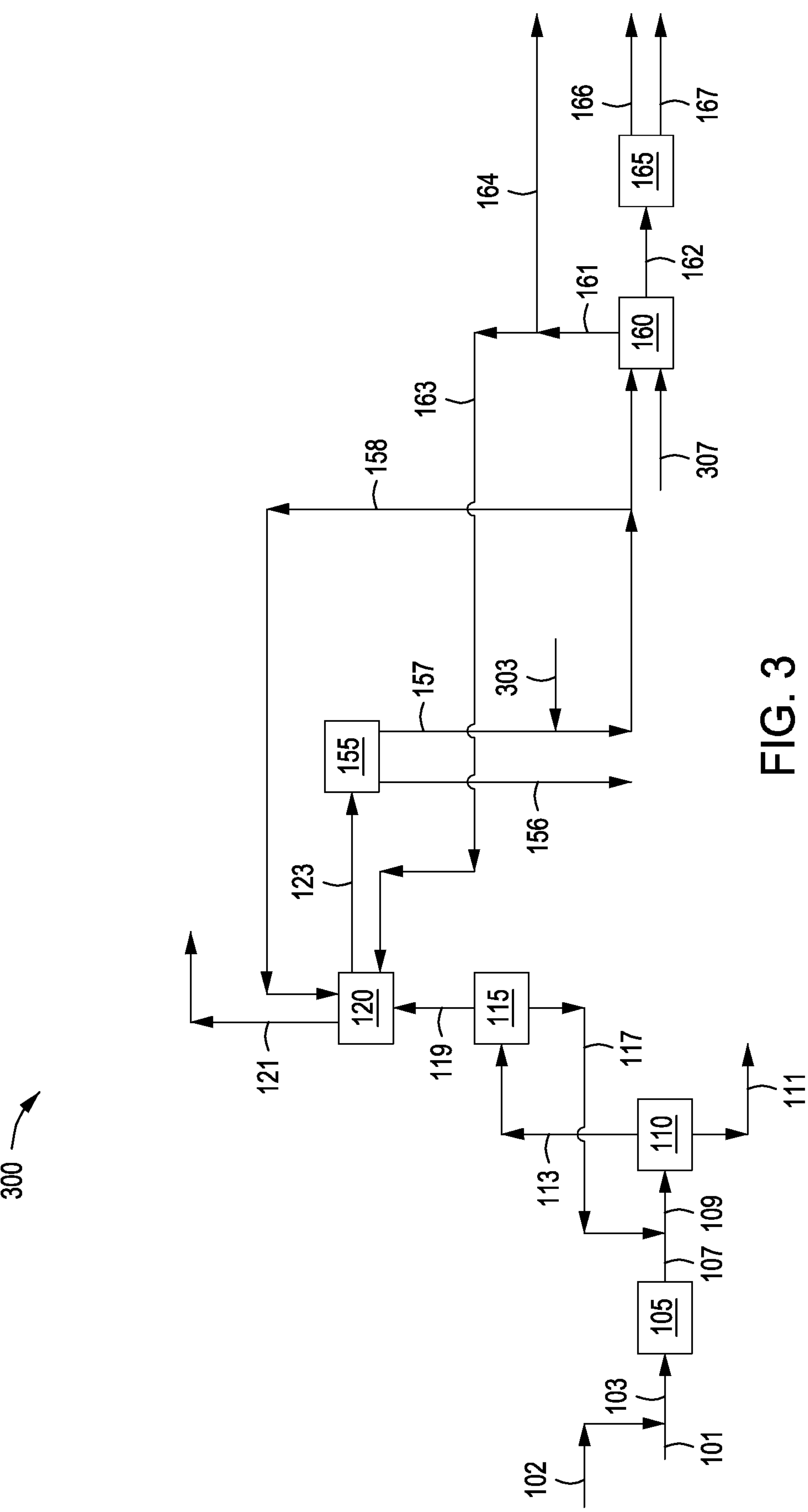
FIG. 3 depicts a schematic of an illustrative system for steam cracking a hydrocarbon feed to produce a steam cracker effluent and accounting for or otherwise handling phenol contained therein, according to one or more embodiments described.

FIG. 3 depicts a schematic of an illustrative system 300 for steam cracking a hydrocarbon feed in line 101 to produce a steam cracker effluent via line 107 and accounting for or otherwise handling phenol contained therein, according to one or more embodiments. The system 300 can include the one or more steam crackers 105, the one or more first separation stages 110, e.g., tar knock-out drum, the one or more second separation stages 115, e.g., primary fractionator, the one or more quench stages 120, the one or more process gas upgrading stages 125, the one or more third separation stages 155, the one or more sour water strippers 160, and the one or more dilution steam generators 165, as described above with reference to FIGS. 1 and 2.

The process gas via line 121 and the naphtha cut via line 123 can be recovered from the quench stage 120 as described above with reference to FIGS. 1 and 2. The process gas in line 121 can include, but is not limited to, a first portion of the phenol and hydrogen, methane, $C_2$ hydrocarbons, $C_3$ hydrocarbons, $C_4$ hydrocarbons, $C_5$ hydrocarbons, or any mixture thereof. The naphtha cut in line 123 can include, but is not limited to, a second portion of the phenol, pygas, and quench medium, e.g., water.

In some examples, prior to introducing the hydrocarbon feed in line 101 into the steam cracker 105, an amount of phenol that will be present in the steam cracker effluent in line 107 can be determined. The amount of phenol that will be present in the steam cracker effluent can be determined, based, at least in part, on a composition of the hydrocarbon feed in line 101, a temperature the hydrocarbon feed will be heated at during steam cracking within the steam cracker 105, a residence time the hydrocarbon feed will be heated at the temperature during steam cracking, or a combination thereof.

It has been discovered that the steam cracker effluent in line 107 will include substantially the same amount of phenol as the hydrocarbon feed in line 101 introduced into the steam cracker 105. Without wishing to be bound by theory, it is believed that while some phenol may be converted within the steam cracker 105 into other compounds, steam cracking produces about the same amount of phenol that may be converted during steam cracking of the hydrocarbon feed. In some examples, if the hydrocarbon feed includes a crude oil containing about 100 ppmw of phenol, the crude oil can be subjected to desalting and/or preheating and the desalted crude oil can include about 60 wt. % to about 80 wt. %, e.g., about 70 wt. %, of the phenol contained in the crude oil. The desalted crude oil can be introduced into the steam cracker 105 and subjected to steam cracking to produce the steam cracker effluent in line 107 that can include about 60 wt. % to about 80 wt. %, e.g., about 70 wt. %, of the phenol present in the hydrocarbon feed in line 101. The phenol contained in the steam cracker effluent in line 107 can include phenol present in the hydrocarbon feed in line 101 and/or phenol produced during steam cracking the hydrocarbon feed in line 101.

With the amount of phenol that will be present in the steam cracker effluent in line 107 determined, the hydrocarbon in line 101 can be mixed, blended, or otherwise combined with steam in line 102 to produce the mixture via line 103 and the mixture can be introduced into the steam cracker 105 and subjected to steam cracking conditions to produce the steam cracker effluent via line 107, as described above. The tar product, the steam cracker quench oil product, and the overhead via lines 111, 117, and 119, respectively can be separated from the steam cracker effluent in line 107. The process gas via line 121 and the naphtha cut via line 123 can be separated from the overhead and the pygas product via line 156 and the aqueous mixture via line 157 can be separated as described above.

In some examples, the aqueous mixture in line 157 can be mixed, blended, or otherwise contacted with a predetermined amount of a dispersant via line 303 to produce a treated aqueous mixture in line 157. The predetermined amount of dispersant can be sufficient to maintain the treated aqueous mixture in line 157 in the form of a solution that includes the phenol. The predetermined amount of dispersant can be sufficient to inhibit, reduce, or prevent the treated aqueous mixture in line 157 from forming an emulsion.

The dispersant in line 303 can be or can include, but is not limited to, non-ionic emulsion breakers. The amount of dispersant in line 303 that can be contacted with the aqueous mixture in line 157 to produce the treated aqueous mixture can be, e.g., from 25, 30, 40, 50, 60, 70, 80, 90, ppm by weight, to 100, 150, 200, 250, 350, 400, ppm by weight, to 410, 420, 440, 450, 460, 480, 500, ppm by weight, based on the total weight of the stream in line 157.

The treated aqueous mixture via line 157 can be introduced into the sour water stripper 160 to produce a sour water stripper overhead or vapor phase product via line 161 and a sour water stripper bottoms or a liquid phase product via line 162. In some examples, the aqueous mixture can be contacted with steam, e.g., counter currently, within the sour water stripper 160, to produce the vapor phase product that can be recovered via line 161. In some examples, at least a portion of the aqueous mixture via line 157 can be recycled to the quench stage via line 158 as the quench medium or a portion of the quench medium. In addition to the vaporized product via line 161, the liquid phase product via line 162 can also be recovered from the steam stripper 160.

In some examples, at least a portion of the vapor phase product in line 161 can be condensed, e.g., via indirect heat exchange or direct contact with a cooling medium such as water, to produce a process water or first process water via line 164. In some examples, a portion of the vapor phase product in line 161 can be recycled via line 163 to the quench stage 120 as at least a portion of the quench medium.

In some examples, the aqueous mixture in line 157 can be mixed, blended, or otherwise contacted with steam and a predetermined amount of an additive via line 307 within the sour water stripper 160 to produce the vapor phase product via line 161 and the liquid phase product via line 162. The predetermined amount of additive can be sufficient to break any emulsion formed in the aqueous mixture in line 157 during contact with the steam. In some examples, the additive in line 307 can be mixed, blended, or otherwise contacted with aqueous mixture in line 157 prior to introducing the aqueous mixture into the sour water stripper 160.

The additive in line 307 can be or can include, but is not limited to, non-ionic emulsion breakers. The amount of additive in line 307 that can be contacted with the aqueous mixture in line 157 and/or within the steam stripper 160 can be, e.g., from 25, 30, 40, 50, 60, 70, 80, 90, ppm by weight, to 100, 150, 200, 250, 350, 400, ppm by weight, to 410, 420, 440, 450, 460, 480, 500, ppm by weight, based on the total weight of the stream in line 157.

In other examples, both a predetermined amount of the dispersant via line 303 and a predetermined amount of the additive via line 307 can be mixed, blended, or otherwise contacted with the aqueous mixture in line 157 and/or within the sour water stripper 160. It should be readily recognized that the predetermined amount of dispersant and the predetermined amount of additive, if used in combination, can be less for each component as compared to using only one or the other alone. The formation of an emulsion can make it difficult to separate the phenol from the steam to cause a majority of the phenol to exit the sour water stripper 160 as a component of the liquid phase product via line 162. Emulsion can cause loss of capacity of the tower which can be monitored by pressure drop at the tower.

The liquid phase product via line 162 can be conducted away from the sour water stripper 160 and can be introduced into the dilution steam generator 165 to produce dilution steam via line 166 and a process water or second process water via line 167, as described above.

In some examples, the vapor phase product in line 161 can include about 5 wt. %, about 7 wt. %, or about 9 wt. % to about 11 wt. %, about 13 wt. %, or about 15 wt. % of the phenol present in n the aqueous mixture in line 157. In some examples, the first process water in line 164 can include about 5 wt. %, about 7 wt. %, or about 9 wt. % to about 11 wt. %, about 13 wt. %, or about 15 wt. % of the phenol present in the aqueous mixture in line 157. In some examples, the first process water in line 164 can include about 2 wt. %, about 4 wt. %, or about 6 wt. % to about 7 wt. %, about 8 wt. %, or about 10 wt. % of the phenol present in the steam cracker effluent in line 107.

In some examples, the liquid phase product in line 162 can include about 85 wt. %, about 87 wt. %, or about 89 wt. % to about 91 wt. %, about 93 wt. %, or about 95 wt. % of the phenol present in the aqueous mixture in line 157. In some examples, the second process water in line 167 can include about 85 wt. %, about 87 wt. %, or about 89 wt. % to about 91 wt. %, about 93 wt. %, or about 95 wt. % of the phenol present in the aqueous mixture in line 157. In some examples, the second process water in line 167 can include about 53 wt. %, about 55 wt. %, or about 57 wt. % to about 60 wt. %, about 63 wt. %, or about 65 wt. % of the phenol present in the steam cracker effluent in line 107.

A mass flow rate of the first process water in line 164 can be about 1%, about 5%, about 10%, about 20%, about 30%, or about 40% to about 60%, about 70%, about 80%, about 90%, or about 100% of a mass flow rate of the vapor phase product in line 161. In some examples, the mass flow rate of the first process water in line 164 can be about 1% to about 20%, about 3% to about 15, about 5% to about 20%, about 10% to about 35%, about 5% to about 15%, about 25% to about 50%, about 40% to about 80%, or about 50% to about 90% of the mass flow rate of the vapor phase product in line 161.

In some examples, a mass flow rate of the first process water in line 164 can be about 1%, about 3%, about 5%, or about 7% to about 10%, about 12%, about 15%, about 17%, or about 20% of a mass flow rate the aqueous mixture in line 157 separated from the naphtha cut in line 123. In other examples, the mass flow rate of the first process water in line 164 can be about 1% to about 20%, about 3% to about 15%, about 5% to about 10% about 4% to about 12%, or about 3% to about 15% the mass flow rate the aqueous mixture in line 157 separated from the naphtha cut in line 123.

In some examples, water can be mixed, blended, or otherwise combined with the first process water in line 164 and/or the second process water in line 167 to produce diluted process water(s). In some examples, the first process water and the second process water, the first diluted process water, and/or the second diluted process water can be combined with one another to produce combined process water. The diluted first process water, the diluted second process water, and/or the diluted combined process water can include ≤100 ppmw, ≤50 ppmw, ≤10 ppmw, ≤5 ppmw, ≤1 ppmw, ≤0.5 ppmw, or ≤0.2 ppmw of phenol, based on a total weight of the first diluted process water, the second diluted process water, or the combined diluted process water.

Figure 4:
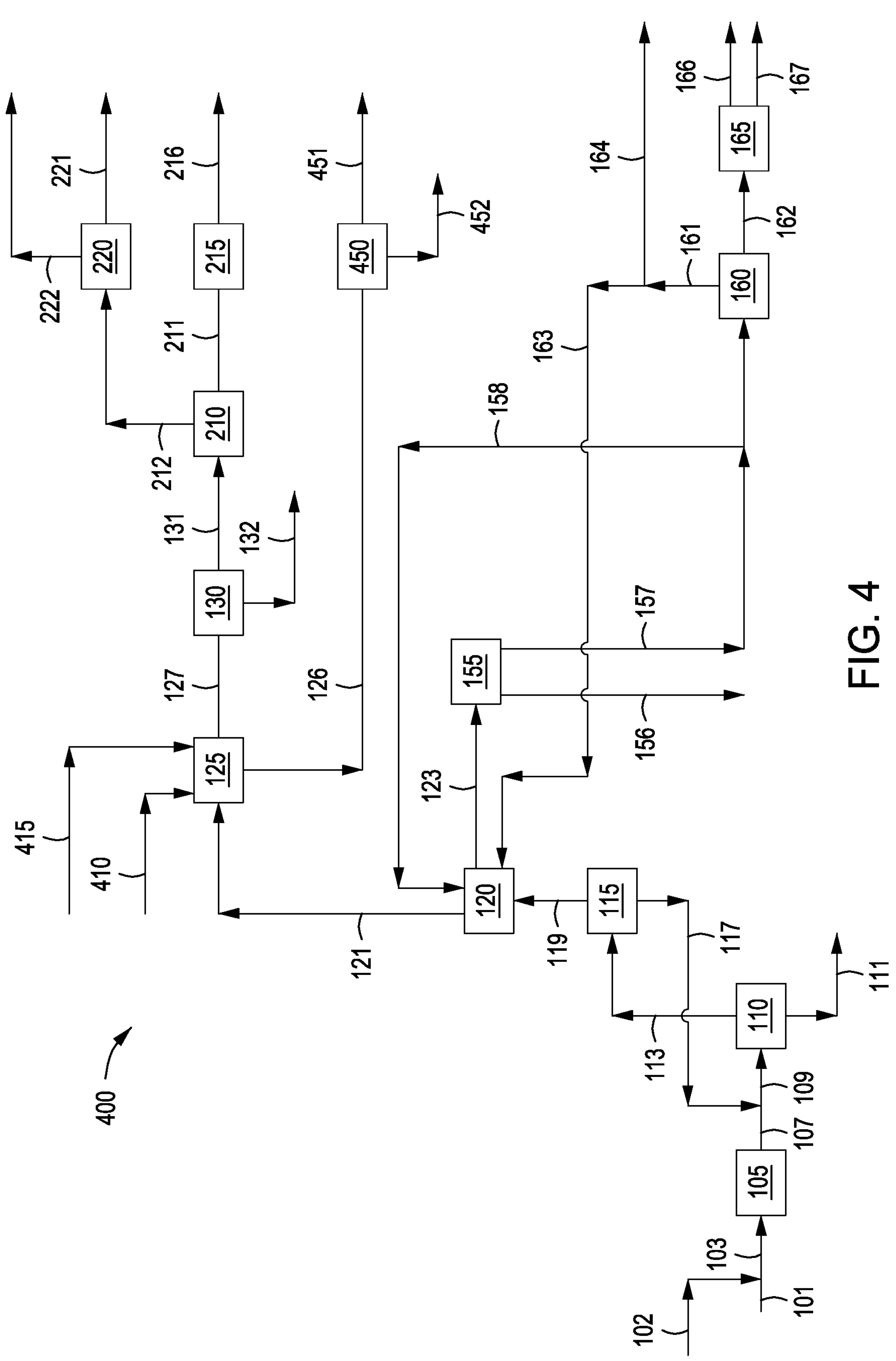
FIG. 4 depicts a schematic of an illustrative system for steam cracking a hydrocarbon feed to produce a steam cracker effluent and accounting for or otherwise handling acetaldehyde contained therein, according to one or more embodiments described.

FIG. 4 depicts a schematic of an illustrative system 400 for steam cracking a hydrocarbon feed in line 101 to produce a steam cracker effluent via line 107 and accounting for or otherwise handling acetaldehyde contained therein, according to one or more embodiments. The system 400 can include the one or more steam crackers 105, the one or more first separation stages 110, the one or more second separation stages 115, the one or more quench stages 120, the one or more process gas upgrading stages 125, the one or more depropanizers 130, the one or more debutanizers 210, the one or more $C_4$ caustic units 220, the one or more hydroprocessing units 215, the one or more third separation stages 155, the one or more sour water strippers 160, and the one or more dilution steam generators 165, as described above with reference to FIG. 2. The system 400 can also include one or more hydroclones 450.

In some examples, prior to introducing the hydrocarbon feed in line 101 into the steam cracker 105, an amount of acetaldehyde that will be present in the steam cracker effluent in line 107 can be determined. The amount of acetaldehyde that will be present in the steam cracker effluent can be determined, based, at least in part, on a composition of the hydrocarbon feed in line 101, a temperature the hydrocarbon feed will be heated at during steam cracking within the steam cracker 105, a residence time the hydrocarbon feed will be heated at the temperature during steam cracking, or a combination thereof.

The hydrocarbon feed in line 101 typically does not include acetaldehyde, which is primarily if not exclusively introduced into the steam cracking process during steam cracking of the hydrocarbon feed in the steam cracker 105. It has been discovered that steam cracking the hydrocarbon feed in line 101 can produce ≥40 ppmw, ≥80 ppmw, ≥80 ppmw, ≥100 ppmw, ≥120 ppmw, ≥150 ppmw, ≥160 ppmw, ≥180 ppmw, ≥200 ppmw; ≥220 ppmw, or ≥240 ppmw, to about 250 ppmw of acetaldehyde. As such, the steam cracker effluent in line 107 can include about 40 ppmw, about 50 ppmw, about 80 ppmw, about 100 ppmw, about 120 ppmw, about 140 ppmw, about 160 ppmw, about 180 ppmw, about 200 ppmw, about 220 ppmw, about 240 ppmw, or about 250 ppmw acetaldehyde, based on the total weight of the steam cracker effluent in line 107. Should the hydrocarbon feed in line 101 be contaminated with acetaldehyde, e.g., similar to how methanol can become a component of the hydrocarbon feed, any acetaldehyde present in the hydrocarbon feed can be readily determined by determining the composition of the hydrocarbon feed in line 101.

In some examples, an amount of a polymer that will be produced within an amine unit by acetaldehyde polymerizing therein can be determined. The amount of polymer that will be produced can be determined, at least in part, on the amount of acetaldehyde that will be present in the steam cracker effluent, process conditions used to separate the process gas and the naphtha cut from the quench stage, and/or process conditions within the process gas upgrading stage 125.

With the amount of acetaldehyde that will be present in the steam cracker effluent in line 107 determined, the hydrocarbon in line 101 can be mixed, blended, or otherwise combined with steam in line 102 to produce the heated mixture via line 103 and the mixture can be introduced into the steam cracker 105 and subjected to steam cracking conditions to produce the steam cracker effluent via line 107, as described above. The tar product, the steam cracker quench oil product, and the overhead via lines 111, 117, and 119, respectively, can be separated from the steam cracker effluent in line 107. The process gas via line 121 and the naphtha cut via line 123 can be separated from the overhead and the pygas product via line 156 and the aqueous mixture via line 157 can be separated as described above.

The process gas in line 121 can include, but is not limited to, a first portion of the acetaldehyde, ethylene, propylene, $C_4$ hydrocarbons, and $C_5$ hydrocarbons. The naphtha cut in line 123 can include, but is not limited to, a second portion of the acetaldehyde, pygas, and water. The process gas in line 121 can include ≥75 wt. %, ≥77 wt. %, ≥78 wt. %, ≥79 wt. %, ≥80 wt. %, ≥82 wt. %, ≥84 wt. %, or ≥86 wt. % of the acetaldehyde present in the steam cracker effluent in line 107. The naphtha cut in line 123 can include ≤23 wt. %, ≤21 wt. %, ≤20 wt. %, ≤18 wt. %, ≤16 wt. %, or ≤14 wt. % of the acetaldehyde present in the steam cracker effluent in line 107.

The process gas can be introduced into the process gas upgrading stage 125 and a third overhead or an upgraded process gas via line 127 and a process water via line 126 can be recovered therefrom. In some examples, an acidic-gas removal solution, e.g., one that can include one or more light amines and/or caustic, can contact the process gas within the process upgrading stage 125. At least a portion of acid gases in the process gas can be transferred to the aqueous amine solution to form a rich amine solution and a process gas that includes less acid gases. In some examples, a water purge or a rich amine purge can be conducted away via line 126 from the process gas upgrading stage 125.

In some examples, a solvent via line 415 can be introduced into the process gas upgrading stage 125 at a predetermined flow rate. The solvent can be capable of dissolving a polymer formed by polymerization of the acetaldehyde within the process gas upgrading unit 125. The predetermined flow rate can be sufficient to dissolve a sufficient amount of the polymer before the polymer causes fouling within the process gas upgrading stage 125.

Suitable solvents that can be introduced via line 415 into the process gas upgrading stage 125 can be or can include, but are not limited to, toluene, steam-cracked gas oil, steam-cracked naphtha, or any mixture thereof.

In some examples, in a given time period, the mass of the solvent introduced into the process gas upgrading unit 125 can be from, e.g., 0.5%, 0.6%, 0.7%, 0.8%, 0.9%, to 1.0%, 1.5%, 2.0%, 2.5%, to 3.0%, 3.5%, 4.0%, 4.5%, or 5.0%, of the mass of the amine introduced via line 415 into the process gas upgrading unit 125.

In some examples, a predetermined amount of a scavenger via line 410 can be introduced into the process gas upgrading stage 125. The scavenger can be capable of limiting polymerization of acetaldehyde within the process gas upgrading stage 125, e.g., amine unit, to below a predetermined amount of polymer. The predetermined amount of polymer can be sufficient to allow the process gas upgrading stage 125 to operate without fouling due to any polymer formed from the acetaldehyde.

Suitable scavengers that can be introduced via line 410 into the process gas upgrading stage 125 can be or can include, but are not limited to, hydroxyl amine sulfates, sodium boron hydride, or any mixture thereof.

In some examples, the predetermined amount of scavenger can be, e.g., from 5, 6, 7, 8, 9, ppm, to 10, 20, 30, 40, to 50, 60, 70, ppm, based on the total weight of stream 121. In other examples, the predetermined amount of scavenger can be, e.g., from 8, 9, 10, 20, or 30, ppm, to 40, 50, 60, 70, or 80, ppm, based on the total weight of stream 107. In other examples, the predetermined amount of scavenger can be, e.g., from 10%, 12%, 15%, 16%, 18%, 20%, to 22%, 24%, 25%, 26%, 28%, 30%, to 32%, 34%, 35%, 36%, 38%, or 40%, by mole, of the amount of acetaldehyde present in stream 121.

In some examples, in lieu of or in addition to introducing the solvent via line 415 and/or the scavenger via line 420 into the process gas upgrading stage 125, the rich amine purge or process water purge via line 126 can be introduced into the hydroclone or separation drum 450. The hydroclone 450 can have a predetermined size that can be sufficient to remove the predetermined amount of polymer from the water purge in line 126. An upgraded rich amine purge via line 451 and a polymer product via line 452 can be recovered from the hydroclone/separation drum 450. Suitable hydroclones and separation drums and operation thereof are described in U.S. Pat. Nos. 6,989,046; 9,321,003; 9,901,845; and 9,593,057.

If the solvent via line 415 is introduced at less than the predetermined flow rate and/or the scavenger via line 420 is introduced at less than the predetermined amount into the process gas upgrading stage 125, the predetermined size of the hydroclone 450 can be reduced to account for the reduction in polymer formation that would be sufficiently addressed by the solvent and/or the scavenger introduced to the purge gas upgrading stage 125.

In some examples, the third overhead or upgraded process gas in line 127 can include ≥1 ppm of acetaldehyde to ≤500 ppm of acetaldehyde. A debutanizer overhead via line 212 can be separated from the third overhead in line 127. For example, the third overhead can be introduced into the depropanizer 130 and the depropanizer overhead via line 131 and the depropanizer bottoms via line 132 can be conducted away therefrom. The depropanizer bottoms can be introduced into the debutanizer 210 and the debutanizer bottoms via line 211 and the debutanizer overhead via line 212 can be recovered therefrom. The process conditions within the debutanizer 210 can be sufficient to cause the debutanizer overhead in line 212 to include ≥90%, ≥92%, ≥94%, ≥96%, ≥98%, or ≥99% of the acetaldehyde present in the depropanizer bottoms. The debutanizer overhead in line 212 can also include ≥90%, ≥92%, ≥94%, ≥96%, ≥98%, or ≥99% of the acetaldehyde present in the upgraded process gas in line 127. The debutanizer overhead via line 212 can be introduced into the $C_4$ caustic unit 220 and contacted with an aqueous caustic solution to produce a spent caustic via line 221 and an acetaldehyde-lean overhead via line 222. In some examples, the spent caustic in line 221 can include ≥95%, ≥96%, ≥97%, or ≥98% of the acetaldehyde present in the debutanizer overhead in line 212.

In some examples, the acetaldehyde-lean overhead via line 222 can be introduced into one or more hydroprocessing stages to produce a hydroprocessed product. In some examples, the debutanizer bottoms via line 211 can be introduced into the hydroprocessing unit 215 to produce the hydroprocessed product via line 216 as described above with reference to FIG. 2.

The naphtha cut via line 123 can be introduced into third separation stage 155 to produce the pygas via line 156 and the aqueous mixture via line 157 as discussed above with reference to FIGS. 1-3. The pygas in line 156 can include about 65 wt. %, about 70 wt. %, or about 73 wt. % to about 77 wt. %, about 80 wt. %, or about 85 wt. % of the acetaldehyde present in the naphtha cut in line 123. The aqueous mixture can include about 15 wt. %, about 20 wt. %, or about 23 wt. % to about 27 wt. %, about 30 wt. %, or about 35 wt. % of the acetaldehyde present in the naphtha cut in line 123. In some examples, the pygas in line 156 can include about 10 wt. %, about 12 wt. %, or about 14 wt. % to about 16 wt. %, about 18 wt. %, or about 20 wt. % of the acetaldehyde present in the steam cracker effluent in line 107. In some examples, the aqueous mixture in line 157 can include about 3.5 wt. %, about 4 wt. %, or about 4.5 wt. % to about 5.5 wt. %, about 6 wt. %, or about 6.5 wt. % of the acetaldehyde present in the steam cracker effluent in line 107.

The aqueous mixture via line 156 can be further processed and/or recycled too the quench stage 125 as discussed above with reference to FIGS. 1-3. For example, the sour water stripper overhead or second vapor phase product via line 161, the process water via line 164, the dilution steam via line 166, and the process water or second process water via line 167 can be produced. In some examples, the process water in line 164 can include about 2 wt. %, about 2.5 wt. %, or about 3 wt. % to about 4 wt. %, about 5 wt. %, or about 6 wt. % of the acetaldehyde preset in the steam cracker effluent in line 107. In some examples the process water in line 167 can include about 0.5 wt. %, about 0.7 wt. %, or about 1 wt. % to about 1.5 wt. %, about 1.7 wt. %, or about 2 wt. % of the acetaldehyde present in the steam cracker effluent in line 107.

In some examples, the process water in line 164 can include about 2 wt. %, about 2.5 wt. %, or about 3 wt. % to about 4 wt. %, about 5 wt. %, or about 6 wt. % of the acetaldehyde preset in the steam cracker effluent in line 107. In some examples the process water in line 167 can include about 0.5 wt. %, about 0.7 wt. %, or about 1 wt. % to about 1.5 wt. %, about 1.7 wt. %, or about 2 wt. % of the acetaldehyde present in the steam cracker effluent in line 107.

In some examples, the process water in line 164 can include about 65 wt. %, about 70 wt. %, or about 73 wt. % to about 77 wt. %, about 80 wt. %, or about 85 wt. % of the acetaldehyde preset in the aqueous mixture in line 157. In some examples the process water in line 167 can include about 15 wt. %, about 20 wt. %, or about 23 wt. % to about 27 wt. %, about 30 wt. %, or about 35 wt. % of the acetaldehyde present in the aqueous mixture in line 157.

In some examples, a mass flow rate of the process water in line 164 can be about 1%, about 5%, about 10%, about 20%, about 30%, or about 40% to about 60%, about 70%, about 80%, about 90%, or about 100% of a mass flow rate of the vapor phase product or second vapor phase product in line 161. In other examples, the mass flow rate of the process water in line 164 can be about 1% to about 20%, about 3% to about 15, about 5% to about 20%, about 10% to about 35%, about 5% to about 15%, about 25% to about 50%, about 40% to about 80%, or about 50% to about 90% of the mass flow rate of the vapor phase product or second vapor phase product in line 161.

In some examples, a mass flow rate of the process water in line 164 can be about 1%, about 3%, about 5%, or about 7% to about 10%, about 12%, about 15%, about 17%, or about 20% of a mass flow rate the aqueous mixture in line 157 separated from the naphtha cut in line 123. In other examples, the mass flow rate of the process water in line 164 can be about 1% to about 20%, about 3% to about 15%, about 5% to about 10% about 4% to about 12%, or about 3% to about 15% the mass flow rate the aqueous mixture in line 157 separated from the naphtha cut in line 123.

Referring to FIGS. 1-4, in some examples, the process water in line 164 can include about 55 wt. % to about 65 wt. % of the methanol, about 8 wt. % to about 18 wt. % of the acetone, about 2 wt. % to about 10 wt. % of the phenol, and about 2 wt. % to about 6 wt. % of the acetaldehyde contained in the steam cracker effluent in line 107. In some examples, the process water in line 167 can include about 5 wt. % to about 15 wt. % of the methanol, about 0.5 wt. % to about 4 wt. % of the acetone, about 53 wt. % to about 65 wt. % of the phenol, and about 0.5 wt. % to about 2 wt. % of the acetaldehyde contained in the steam cracker effluent in line 107. In some examples, the process gas in line 121 can include about 25 wt. % to about 35 wt. % of the methanol, ≥30 wt. % of the acetone, ≥1 wt. % of the phenol, and ≥75 wt. % of the acetaldehyde contained in the steam cracker effluent in line 107. In some examples, the pygas in line 156 can include ≤1 wt. % of the methanol, about 50 wt. % to about 60 wt. % of the acetone, about 20 wt. % to about 30 wt. % of the phenol, and about 10 wt. % to about 20 wt. % of the acetaldehyde contained in the steam cracker effluent in line 107.

In other examples, the process water in line 164 can include about 55 wt. % to about 65 wt. % of the methanol, about 8 wt. % to about 18 wt. % of the acetone, about 2 wt. % to about 10 wt. % of the phenol, and about 2 wt. % to about 6 wt. % of the acetaldehyde contained in the steam cracker effluent in line 107, the process water in line 167 can include about 5 wt. % to about 15 wt. % of the methanol, about 0.5 wt. % to about 4 wt. % of the acetone, about 53 wt. % to about 65 wt. % of the phenol, and about 0.5 wt. % to about 2 wt. % of the acetaldehyde contained in the steam cracker effluent in line 107, the process gas in line 121 can include about 25 wt. % to about 35 wt. % of the methanol, ≤30 wt. % of the acetone, ≤1 wt. % of the phenol, and ≥75 wt. % of the acetaldehyde, and the pygas in line 156 can include ≤1 wt. % of the methanol, about 50 wt. % to about 60 wt. % of the acetone, about 20 wt. % to about 30 wt. % of the phenol, and about 10 wt. % to about 20 wt. % of the acetaldehyde contained in the steam cracker effluent in line 107.

It should be understood that any given system 100, 200, 300, and 400, e.g., 300, described herein can include any one or more additional process units or stages described with reference to one or more of the other systems, e.g., 100, 200, and/or 400. It should also be understood that well-known process equipment or units have been left out for simplicity and ease of description. For example, the systems 100, 200, 300, and/or 400 can include a number of compressors, pumps, reboilers, heat exchangers, storage tanks, etc., which are readily apparent those skilled in the art.

This disclosure can further include the following aspects/embodiments:

A1. A process for upgrading a hydrocarbon, comprising:

determining an amount of methanol that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof; and introducing a sufficient amount of a first sorbent into a first methanol sorbent unit to allow the first methanol sorbent unit to process a depropanizer overhead that is to be separated from the steam cracker effluent for at least as long as a predetermined period of time without requiring replacement or re-activation of the first sorbent due to saturation caused by methanol present in the depropanizer overhead.

A2. The process of A1, further comprising:

steam cracking a hydrocarbon feed comprising methanol to produce a steam cracker effluent comprising cracked hydrocarbons and methanol;

separating a process gas comprising methanol, ethane, ethylene, propane, and propylene from the steam cracker effluent;

separating the depropanizer overhead from the process gas; and introducing the depropanizer overhead into the first methanol sorbent unit for at least as long as the predetermined period of time and recovering a treated depropanizer overhead.

A3. The process of A2, wherein the treated depropanizer overhead comprises less methanol than the depropanizer overhead.

A4. The process of A3, further comprising:

introducing a sufficient amount of a second sorbent into a second methanol sorbent unit to allow the second methanol sorbent unit to process a deethanizer bottoms that is to be separated from the treated depropanizer overhead for at least as long as the predetermined period of time without requiring replacement or re-activation of the second sorbent due to saturation caused by methanol present in the deethanizer bottoms;

separating the deethanizer bottoms from the treated depropanizer overhead; and introducing the deethanizer bottoms into the second methanol sorbent unit for at least as long as the predetermined period of time.

A5. The process of any of A2 to A4, further comprising:

separating a naphtha cut comprising pygas, water, and methanol from the steam cracker effluent, wherein an amount of methanol in the naphtha cut is greater than an amount of methanol in the process gas;

separating a pygas product and an aqueous mixture comprising methanol from the naphtha cut;

contacting the aqueous mixture with steam to heat the aqueous mixture and produce a vapor phase product and a liquid phase product; and condensing at least a portion of the vapor phase product to produce a process water, wherein >50% of the methanol contained in the steam cracker effluent is present in the process water, and wherein <50% of the methanol contained in the steam cracker effluent is present in the process gas.

A6. The process of any of A1 to A5, wherein the first sorbent and the second sorbent are each an adsorbent.

A7. The process of any of A1 to A6, wherein the first sorbent and the second sorbent each comprises at least one metal from Group 1, 10, or 11 of the periodic table of elements or an oxide thereof.

A8. The process of any of A1 to A7, wherein the predetermined period of time is at least 5 days.

A9. A process for upgrading a hydrocarbon, comprising:

steam cracking a hydrocarbon feed comprising methanol to produce a steam cracker effluent comprising cracked hydrocarbons and methanol;

separating a process gas and a naphtha cut from the steam cracker effluent, wherein the process gas comprises ethylene, propylene, and ≤40 wt. % of the methanol in the steam cracker effluent, and wherein the naphtha cut comprises ≥60 wt. % of the methanol in the steam cracker effluent;

separating a pygas product and an aqueous mixture from the naphtha cut, wherein the aqueous mixture comprises ≥95 wt. % of the methanol in the naphtha cut;

contacting the aqueous mixture with steam to produce a vapor phase product comprising ≥80 wt. % of the methanol in the aqueous mixture and a liquid phase product comprising ≤20 wt. % of the methanol in the aqueous mixture;

cooling at least a portion of the vapor phase product to produce a first waste water, wherein ≥50 wt. % of the methanol contained in the steam cracker effluent is present in the first process water.

A10. The process of A9, wherein the hydrocarbon feed comprises a desalted crude oil derived from a raw crude oil comprising methanol, and wherein the desalted crude oil comprises about 60 wt. % to about 80 wt. % of the methanol present in the raw crude oil.

A11. The process of A9 or A10, wherein a mass flow rate of the first process water removed from the process is about 1% to about 100% of a mass flow rate of the vapor phase product.

A12. The process of any of A9 to A11, wherein a mass flow rate of the first process water removed from the process is about 5% to about 10% of a mass flow rate the aqueous mixture separated from the naphtha cut.

A13. The process of any of A9 to A12, further comprising;

heating the liquid phase product to produce dilution steam; and separating a second process water from the dilution steam, wherein ≤50 wt. % of the methanol contained in liquid phase product is present in the second process water.

A14. The process of A13, wherein:

the first process water removed from the process comprises about 20 wt. % to about 65 wt. % of the methanol contained in the steam cracker effluent, the second process water comprises about 1 wt. % to about 15 wt. % of the methanol contained in the steam cracker effluent, and the process gas comprises about 25 wt. % to about 35 wt. % of the methanol contained in the steam cracker effluent.

A15. A process for upgrading a hydrocarbon, comprising:

steam cracking a hydrocarbon feed to produce a steam cracker effluent comprising acetone:

separating a process gas and a naphtha boiling range stream from the steam cracker effluent, wherein the process gas comprises a first portion of the acetone, $C_2$ hydrocarbons, $C_3$ hydrocarbons, $C_4$ hydrocarbons, and $C_5$ hydrocarbons, and wherein the naphtha boiling range stream comprises a second portion of the acetone, pygas, and water;

contacting the process gas with an aqueous amine, an aqueous inorganic base, or an aqueous amine and an aqueous inorganic base to produce a first process water comprising a third portion of the acetone and an upgraded process gas comprising a fourth portion of the acetone, wherein an amount of the third portion of acetone in the first process water is greater than an amount of the fourth portion of acetone in the upgraded process gas;

separating a depropanizer bottoms from the upgraded process gas, wherein the depropanizer bottoms comprises the fourth portion of acetone, the $C_4$ hydrocarbons, and the $C_5$ hydrocarbons;

introducing the depropanizer bottoms into a debutanizer; and recovering a debutanizer overhead comprising the $C_4$ hydrocarbons and a debutanizer bottoms comprising the $C_5$ hydrocarbons from the debutanizer, wherein process conditions within the debutanizer are controlled to cause ≥60 wt. % of the acetone in the depropanizer bottoms to exit the debutanizer with the debutanizer bottoms.

A16. The process of A15, further comprising:

hydroprocessing the debutanizer bottoms to produce a hydrogenated product.

A17. The process of A15 or A16, further comprising, contacting the debutanizer overhead with an aqueous caustic solution to produce a caustic treated overhead and a water purge, wherein the water purge comprises at least a portion of any acetone in the debutanizer overhead.

A18. The process of any of A15 to A17, wherein the process conditions within the debutanizer are controlled to cause ≥67 wt. % of the acetone in the depropanizer bottoms to exit the debutanizer with the debutanizer bottoms.

A19. The process of any of A15 to A18, wherein the amount of acetone in the first process water is ≥55 wt. %, based on a total weight of acetone in the process gas.

A20. The process of any of A15 to A19, wherein the debutanizer overhead comprises butadiene, and wherein at least a portion of the butadiene is removed by contacting the debutanizer overhead with an extraction solvent comprising dimethylforamide, acetonitrile, N-methyl pyrolidone, or a mixture thereof.

A21. The process of any of A15 to A20, further comprising:

separating a pygas product and an aqueous mixture from the naphtha boiling range stream contacting the aqueous mixture with steam to produce a vapor phase product;

cooling at least a portion of the vapor phase product to produce a first process water; and removing the first process water from the process, wherein ≥50 wt. % of the acetone contained in aqueous mixture is present in the second process water.

A22. A process for upgrading a hydrocarbon, comprising:

determining an amount of phenol that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof;

steam cracking the hydrocarbon feed to produce a steam cracker effluent;

separating a process gas and a naphtha boiling range stream from the overhead, wherein the naphtha boiling range stream comprises a pygas, water, and phenol;

separating a pygas product and an aqueous mixture comprising the phenol from the naphtha boiling range stream; and contacting the aqueous mixture with a predetermined amount of a dispersant to produce a treated aqueous mixture, wherein the predetermined amount of dispersant is sufficient to maintain the aqueous mixture in the form of a solution comprising the phenol.

A23. The process of A22, wherein the hydrocarbon feed comprises a desalted crude oil derived from a raw crude oil comprising methanol, and wherein the desalted crude oil comprises about 60 wt. % to about 80 wt. % of the methanol present in the raw crude oil.

A24. The process of A22 or A23, wherein the dispersant comprises a non-ionic emulsion breaker.

A25. The process of A24, wherein the dispersant is used at an amount from 25 to 500 ppm by weight, based on the total weight of the aqueous mixture.

A26. A process for upgrading a hydrocarbon, comprising:

steam cracking a hydrocarbon feed comprising phenol to produce a steam cracker effluent comprising cracked hydrocarbons and phenol;

separating a tar product, a steam cracker quench oil product, and an overhead from the steam cracker effluent;

separating a process gas and a naphtha cut from the overhead, wherein the process gas comprises ethylene, propylene, and ≤3 wt. % of the phenol in the steam cracker effluent, and wherein the naphtha cut comprises pygas, water, and ≥97 wt. % of the phenol in the steam cracker effluent;

separating a pygas product and an aqueous mixture from the naphtha cut, wherein the pygas product comprises ≤40 of the phenol in the naphtha cut, and wherein the aqueous mixture comprises ≥60 wt. % of the phenol in the naphtha cut:

contacting the aqueous mixture with steam and a predetermined amount of an additive to produce a vapor phase product comprising about 5 wt. % to about 15 wt. % of the phenol in the aqueous mixture and a liquid phase product comprising about 85 wt. % to about 95 wt. % of the phenol in the aqueous mixture, wherein the predetermined amount of additive is sufficient to break any emulsion formed in the aqueous mixture during contact with the steam; cooling at least a portion of the vapor phase product to produce a first process water comprising about 4 wt. % to about 8 wt. % of the phenol contained in the steam cracker effluent; heating the liquid phase product to produce dilution steam; and separating a second process water from the dilution steam, wherein the second process water comprises about ≥20 wt. % of the phenol contained in the steam cracker effluent.

A27. The process of A26, wherein the hydrocarbon feed comprises a desalted crude oil, and wherein the hydrocarbon feed comprises about 60 wt. % to about 80 wt. % of any phenol present in the crude oil prior to desalting.

A28. The process of A26 or A27, further comprising mixing water with the second process water to produce a diluted process water.

A29. The process of any of A26 to A28, wherein a mass flow rate of the first process water is about 1% to about 100% of a mass flow rate of the vapor phase product.

A30. The process of any of A26 to A29, wherein the first process water is removed from the process at a mass flow rate that is about 5% to about 10% of a mass flow rate the aqueous mixture is separated from the naphtha boiling range stream.

A31. A process for upgrading a hydrocarbon, comprising:

determining an amount of acetaldehyde that will be present in a steam cracker effluent based, at least in part, on a composition of a hydrocarbon feed to be steam cracked, a temperature the hydrocarbon feed will be heated at during steam cracking, a residence time the hydrocarbon feed will be heated at the temperature during steam cracking, or a combination thereof;

determining an amount of polymer that will be produced within an amine unit by acetaldehyde polymerizing therein, based at least in part on the determined amount of acetaldehyde that will be present in the steam cracker effluent;

steam cracking the hydrocarbon feed to produce a steam cracker effluent comprising acetaldehyde;

separating a process gas and a naphtha cut from the steam cracker effluent, wherein the process gas comprises a first portion of the acetaldehyde, ethylene, propylene, $C_4$ hydrocarbons, and $C_5$ hydrocarbons, and wherein the naphtha cut comprises a second portion of the acetaldehyde, pygas, and water;

introducing the process gas into an amine unit;

contacting the process gas with an aqueous amine solution within the amine unit; and introducing a solvent into the amine unit at a predetermined flow rate, wherein the solvent is capable of dissolving the determined amount of polymer that will be produced within the amine unit, and wherein the predetermined flow rate is sufficient to dissolve a sufficient amount of the polymer before the polymer causes fouling within the amine unit;

introducing a predetermined amount of a scavenger into the amine unit, wherein the scavenger limits polymerization of acetaldehyde within the amine unit to below a predetermined amount of polymer, and wherein the predetermined amount of polymer allows the amine unit to operate without fouling due to any polymer formed from the acetaldehyde;

introducing a rich amine purge from the amine unit into a hydroclone or a separation drum having a predetermined size, wherein the predetermined size of the hydroclone is sufficient to remove the determined amount of polymer from the rich amine; or a combination thereof.

A32. The process of A31, further comprising:

recovering a third overhead from the amine unit comprising acetaldehyde at a concentration from 1 ppm to 500 ppmw, based on the total weight of the third overhead;

separating a debutanizer overhead from the third overhead, wherein the debutanizer overhead comprises ≥90 wt. % of the acetaldehyde in the third overhead; and contacting the debutanizer overhead with an aqueous caustic solution to produce a spent caustic and an acetaldehyde-lean overhead, wherein the spent caustic comprises ≥95 wt. % of the acetylene in the debutanizer overhead.

A33. The process of A32, wherein the solvent is introduced into the amine unit at the predetermined flow rate.

A34. The process of A32, wherein the predetermined amount of a scavenger is introduced into the amine unit.

A35. The process of A32, wherein the process water purge from the amine unit is introduced into the hydroclone or the separation drum having the predetermined size.

A36. The process of any of A1 to A35, wherein the hydrocarbon feed has a total acid number of ≥0.5 mg KOH/g of hydrocarbon feed, as measured according to ASTM D664-18e2.

A37. The process of any of A1 to A35, wherein the hydrocarbon feed has a total acid number of ≥1.5 mg KOH/g of hydrocarbon feed, as measured according to ASTM D664-18e2.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:

steam cracking a hydrocarbon feed comprising methanol to produce a steam cracker effluent comprising cracked hydrocarbons and methanol;

separating a process gas and a naphtha cut from the steam cracker effluent, wherein the process gas comprises ethylene, propylene, and ≤40 wt. % of the methanol in the steam cracker effluent, and wherein the naphtha cut comprises ≥60 wt. % of the methanol in the steam cracker effluent;

separating a pygas product and an aqueous mixture from the naphtha cut, wherein the aqueous mixture comprises ≥95 wt. % of the methanol in the naphtha cut;

contacting the aqueous mixture with steam to produce a vapor phase product comprising ≥80 wt. % of the methanol in the aqueous mixture and a liquid phase product comprising ≤20 wt. % of the methanol in the aqueous mixture;

cooling at least a portion of the vapor phase product to produce a first process water, wherein ≥50 wt. % of the methanol contained in the steam cracker effluent is present in the first process water.

2. The process of claim 1, wherein the hydrocarbon feed comprises a desalted crude oil derived from a raw crude oil comprising methanol, and wherein the desalted crude oil comprises about 60 wt. % to about 80 wt. % of the methanol present in the raw crude oil.

3. The process of claim 1, wherein a mass flow rate of the first process water removed from the process is about 1% to about 100% of a mass flow rate of the vapor phase product.

4. The process of claim 1, wherein a mass flow rate of the first process water removed from the process is about 5% to about 10% of a mass flow rate the aqueous mixture separated from the naphtha cut.

5. The process of claim 1, further comprising;

heating the liquid phase product to produce dilution steam; and separating a second process water from the dilution steam, wherein ≤50 wt. % of the methanol contained in liquid phase product is present in the second process water.

6. The process of claim 5, wherein:

the first process water removed from the process comprises about 20 wt. % to about 65 wt. % of the methanol contained in the steam cracker effluent, the second process water comprises about 1 wt. % to about 15 wt. % of the methanol contained in the steam cracker effluent, and the process gas comprises about 25 wt. % to about 35 wt. % of the methanol contained in the steam cracker effluent.

* * * * *